United States Patent [19]

Manos et al.

[11] Patent Number: 5,447,839
[45] Date of Patent: Sep. 5, 1995

[54] DETECTION OF HUMAN PAPILLOMAVIRUS BY THE POLYMERASE CHAIN REACTION

[75] Inventors: M. Michele Manos, Richmond; Heidi M. Bauer; Catherine E. Greer, both of Oakland; Robert M. Resnick, Richmond; Yi Ting, Berkeley, all of Calif.

[73] Assignee: Hoffmann-La Roche Inc., Nutley, N.J.

[21] Appl. No.: 50,743

[22] Filed: Apr. 20, 1993

Related U.S. Application Data

[63] Continuation of Ser. No. 613,142, Nov. 14, 1990, abandoned, which is a continuation-in-part of Ser. No. 3,747, Sep. 9, 1989, Pat. No. 5,283,171, which is a continuation-in-part of Ser. No. 322,550, Mar. 10, 1989, Pat. No. 5,182,377, which is a continuation-in-part of Ser. No. 243,486, Sep. 9, 1988, abandoned.

[51] Int. Cl.$^6$ .......................... C12Q 1/68; C07H 21/04
[52] U.S. Cl. ......................................... 435/5; 435/91.2; 435/6; 436/501; 536/23.1; 536/24.3; 536/24.31; 536/24.32; 536/24.33; 935/77; 935/78; 935/88
[58] Field of Search .......................... 435/5, 6, 91.2; 436/501; 536/23.1, 24.31, 24.32, 24.33, 24.3; 935/7, 78, 88

[56] References Cited

U.S. PATENT DOCUMENTS

| | | | |
|---|---|---|---|
| 4,849,331 | 7/1989 | Lorinez | 435/5 |
| 4,849,332 | 7/1989 | Lorinez | 435/5 |
| 4,849,334 | 7/1989 | Lorinez | 435/5 |
| 4,908,306 | 3/1990 | Lorincz | 435/5 |
| 4,983,728 | 1/1991 | Herzog et al. | 536/27 |
| 5,057,411 | 10/1991 | Lancaster et al. | 435/6 |

FOREIGN PATENT DOCUMENTS

| | | |
|---|---|---|
| 0354440 | 1/1989 | European Pat. Off. |
| 0425995 | 5/1991 | European Pat. Off. |
| 8605816 | 10/1986 | WIPO |
| 8806634 | 9/1988 | WIPO |
| 8902934 | 4/1989 | WIPO |
| 8909940 | 10/1989 | WIPO |
| 9108313 | 6/1991 | WIPO |

OTHER PUBLICATIONS

Murakawa et al. (1988) DNA, vol. 7, No. 4, pp. 287–295.
Cheyrou et al., 1988, *J. Clin. Chem. Clin. Biochem.* 26(5):290.
Broker and Botchan, 1986, *Cancer Cells* 4:17–36.
Broker and Chow, 1986, *Cancer Cells* 4:589–594.
Caussy et al., 1988, *J. Clinical Microbiology* 26(2)236–243.
Chow et al., 1987, *Cancer Cells* 5:55–72.
Cole et al., 1986, *J. Virology* 58(3):991–993.
Cornelissen et al., 1988, *J. Medical Virology* 25:105–114.
Shibata et al., 1988, *J. Exp. Med.* 167:225–230.
Webb et al., 1987, *J. Inf. Disease* 156(6):912–919.
Shibata et al., 1989, *Diagn. Cytopthol.* 5(1):40–43.
Kiyabu et al., 1989, *Am. J. Surg. Pathol.* 13(3):221–224.
*Papillomaviruses; Papovaviradae: Volt* ed; Salzman and Howley (1987) Plenum Press New York.
Manos et al., 1989, *Cancer Cells* 7:209–214.
Meanwell, 1988, Cancer Survey 7:482–497.
Shibata et al., 1988, *Lab Invest.* 59:555–559.
Schwarz et al., 1983, *EMBO J* 2:2341.

(List continued on next page.)

*Primary Examiner*—Stephanie W. Zitomer
*Assistant Examiner*—Ardin H. Marschel
*Attorney, Agent, or Firm*—George M. Gould; Dennis P. Tramaloni; Stacey R. Sias

[57] ABSTRACT

The presence of human papillomavirus (HPV) in a sample can be detected and the HPV typed by a method that involves the amplification of HPV DNA sequences by the polymerase chain reaction (PCR). The primers used in the method are consensus primers that can be used to amplify a particular region of the genome of any HPV. The presence of HPV in a sample is indicated by the formation of amplified DNA. The HPV nucleic acid is detected by consensus probes that may be short oligonucleotide probes or long genetic probes. The HPV is typed by the use of type-specific DNA probes specific for the amplified region of DNA.

8 Claims, No Drawings

OTHER PUBLICATIONS

Seedorf et al., 1985, *Virology* 145:181.
Cole and Danos, 1987, *J. Mol. Biol.* 193:599.
Dartmann et al., 1986, *Virology* 151:124.
Campione-Piccardo et al., "Type-Specific Identification of HPV Associated with Genital Lesions after Group-Specific Sequence Amplification," (Abstract) VIIth Intl. Papillomavirus Workshop, Cote d'Azur, France, May 16–20, 1988.
Cornelisson, et al., "Detection of HPV DNA by PCR," (Abstract) VIIth Intl. Papillomavirus Workshop, Cote d'Azur, France, May 16–20, 1988.
Evander, et al., "Specific Amplification of HPV DNA from Clinical Specimens," (Abstract) VIIIth Intl. Papillomavirus Workshop, Cote d'Azur, France, May 16–20, 1988.
Kasher, et al., "Alterations in the HPV 6 LCR Generated during Propagation in *E. coli* and Determination of Authentic Sequences by Genomic Amplification," (Abstract) VIIth Intl. Papillomavirus Workshop, Cote d'Azur, France, May 16–20, 1988.
Kashima, et al., "HPV–DNA in Oral Squamous Cell Carcinoma and Oral Leukoplakia," (Abstract) VIIIth Intl. Papillomavirus Workshop, Cote d'Azur, France, May 16–20, 1988.
Maitland, et al., "Human Papillomavirus in Biopsies of Oral Tissue," (Abstract) VIIth Intl. Papillomavirus Workshop, Cote d'Azur, France, May 16–20, 1988.
Melchers, et al., "Diagnosis of HPV Infections in Cervical Scrapes," (Abstract) VIIth Intl. Papillomavirus Workshop, Cote d'Azur, France, May 16–20, 1988.
Rotenberg, et al., "Generation of HPV-11 E1 E4 and E1 E2 cDNAs through the Use of a Retroviral Vector," (Abstract) VIIth Intl. Papillomavirus Workshop, Cote d'Azur, France, May 16–20, 1988.
Shah, et al., "Papillomavirus Types and Progression of Carcinoma in situ of the Cervix to Invasive Cancer," (Abstract) VIIth Intl. Papillomavirus Workshop, Cote d'Azur, France, May 16–20, 1988,
Smith, et al., "Comparison of HPV Screening Tests for Early Detection of Genital Cancers," (Abstract) VIIth Intl. Papillomavirus Workshop, Cote d'Azur, France, May 16–20, 1988.
Young, et al., "Detection of HPV in Cervical Smear Cells Using PCR,"](Abstract) VIIth Intl. Papillomavirus Workshop, Cote d'Azur, France, May 16–20, 1988.
McNichol and Dodd, "Human Papillomavirus Infection of the Prostate Gland," VIth Intl. Papillomavirus Workshop, Washington, D.C., Jun. 14–18, 1987.
Benedict, 1988, *West. J. Med.* 149(5):597–598.
Dallas, 1989, *J. Med. Virol.* 27:105–111.
Griffin et al., 1989, *J. Pathol.* 157:176.
Huang, 1988, *West. J. Med* 149(5)597.
Kiyabu et al., 1989, *Am. J. Surg. Pathol.* 13(3):221–224.
Manos et al., abstract presented at "HPV's and Squamous Carcinoma" conference, Oct. 24–26, 1988.
Melchers et al., 1989, *J. Clin. Microb.* 27:329–335.
Melchers et al., 1989, *J. Med. Virol.* 27:329–335.
Morris et al., Dec. 10, 1988, *Lancet* p. 1368.
Shibata et al., 1989. *DigsnosticCytopathology* 5(1):40–43.
Tidy et al., Feb. 25, 1989, *Lancet* p. 434.
Xiao et al., Oct. 15, 1988, *Lancet* p. 902.
Xiao and Yen, 1989, *Lab. Invest.* 60(1):107A.
Young et al., 1989, *Br. Med. J.* 298:14–18.
de Villiers, 1989, J. Virol. 63(11):4898–4903.
Goldsborough et al., 1989, Virology 171:306–311.
Maitland et al., 1989, Br. J. Cancer 59:698–703.
McDonnell et al., 1989, N. Engl. J. Med. 320(22):1442–1446.
Melchers et al., 1989, J. Clin. Microb. 27(8):1711–1714.
Resnick et al., 1990, JNCI 82(18):1477–1484.
Roman and Fife, 1989, Clin. Microbiol. Rev. 2(2):166–190.
Tidy et al., Jun. 3, 1989, Lancet 1(8649):1225–1227.
van den Brule et al., 1989, J. Med. Virol. 29:20–27.
Snijders et al., 1990, J. Gen. Virol. 71:173–181.
van den Brule et al., 1990, Int. J. Cancer 45:644–649.
van den Brule et al., 1990, J. Clin. Microbiol. 28(12):2739–2743.
Bauer et al., 1991, JAMA 265(4):472–477.
Shibata, 1987, Am. J. Clin. Path. 88:524.
1989, Lancet 8646(1):1051–1052.

SEQUENCE LISTING ( 1 ) GENERAL INFORMATION:

( i i i ) NUMBER OF SEQUENCES: 85

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

CATTTGTTGG GGTAACCAAC        20

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

TAGGTCTGCA GAAAACTTTT C        21

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

TGTTTGCTGG CATAATCAAT        20

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

TAAGTCTAAA GAAAACTTTT C        21

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

CATATGCTGG GGTAATCAGG                                                          2 0

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

CAGGTCTGCA GAAAAGCTGT                                                          2 0

( 2 ) INFORMATION FOR SEQ ID NO:7:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

TATTTGTTGG GGCAATCAG                                                            1 9

( 2 ) INFORMATION FOR SEQ ID NO:8:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

CTAAATCTGC AGAAAACTTT T                                                      2 1

( 2 ) INFORMATION FOR SEQ ID NO:9:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

CTGTGGTAGA TACCAC W CGC AGTAC                                        2 5

( 2 ) INFORMATION FOR SEQ ID NO:10:

( i ) SEQUENCE CHARACTERISTICS:
        ( A ) LENGTH: 22 base pairs
        ( B ) TYPE: nucleic acid
        ( C ) STRANDEDNESS: single (D) TOPOLOGY: linear (ii) MOLECULE TYPE: DNA (genomic)

(xi) SEQUENCE DESCRIPTION: SEQ ID NO:10:

ACAATGAATC CYTCTGTTTT GG　　　　　　　　　　　　　　　　　　　　　　　　22

(2) INFORMATION FOR SEQ ID NO:11:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

ATCGCCTCCM CCAAATG　　　　　　　　　　　　　　　　　　　　　　　　　　17

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

ACATACACCT CCAGCACCTA　　　　　　　　　　　　　　　　　　　　　　　　20

(2) INFORMATION FOR SEQ ID NO:13:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

CATACACCTC CAGCACCTA　　　　　　　　　　　　　　　　　　　　　　　　　19

(2) INFORMATION FOR SEQ ID NO:14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

GATATGGCAG CACATAATGA C　　　　　　　　　　　　　　　　　　　　　　　21

(2) INFORMATION FOR SEQ ID NO:15:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

AGTTTCTGAA GTAGATATGG CA　　　　　　　　　　　　　　　　　　　　　　22

( 2 ) INFORMATION FOR SEQ ID NO:16:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

CTGAAGTAGA TATGGCAGCA C                              21

( 2 ) INFORMATION FOR SEQ ID NO:17:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

GTAACATCCC AGGCAATTG                                19

( 2 ) INFORMATION FOR SEQ ID NO:18:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

GATGCTGCAC CGGCTGAA                                 18

( 2 ) INFORMATION FOR SEQ ID NO:19:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

GCCCAGGTAC AGGAGAC                                  17

( 2 ) INFORMATION FOR SEQ ID NO:20:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

GGGCAATATG ATGCTACCAA T                              21

( 2 ) INFORMATION FOR SEQ ID NO:21:

( i ) SEQUENCE CHARACTERISTICS:
        ( A ) LENGTH: 19 base pairs
        ( B ) TYPE: nucleic acid (C) STRANDEDNESS: single
        (D) TOPOLOGY: linear (ii) MOLECULE TYPE: DNA (genomic)

(xi) SEQUENCE DESCRIPTION: SEQ ID NO:21:

GTACCTGGGC AATATGATG								19

(2) INFORMATION FOR SEQ ID NO:22:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

TCTCCTGTAC CTGGGCAA								18

(2) INFORMATION FOR SEQ ID NO:23:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

TCAGCCGGTG CAGCATCC								18

(2) INFORMATION FOR SEQ ID NO:24:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

GAGGGAGGTG TGGTCAAT								18

(2) INFORMATION FOR SEQ ID NO:25:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

AAGAACCTGA GGGAGGT								17

(2) INFORMATION FOR SEQ ID NO:26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

CCAAAAGCCY AAGGAAGATC                                                            20

(2) INFORMATION FOR SEQ ID NO:27:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

ACCACACCTC CCTCAG                                                                16

(2) INFORMATION FOR SEQ ID NO:28:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

ACAGGCCATT ACATGTCAA                                                             19

(2) INFORMATION FOR SEQ ID NO:29:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

CTGCTGTGTC TTCTAGTGAC AG                                                         22

(2) INFORMATION FOR SEQ ID NO:30:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

TGCACCAAAA CCTAAAGATG                                                            20

(2) INFORMATION FOR SEQ ID NO:31:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

ATCATCTTTA GGTTTTGGTG C                                                          21

(2) INFORMATION FOR SEQ ID NO:32:

(i) SEQUENCE CHARACTERISTICS:
        (A) LENGTH: 22 base pairs (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:32:

TAGAGTCTTC CATACCTTCT AC 22

(2) INFORMATION FOR SEQ ID NO:33:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:33:

CTGTAGCTCC TCCACCATCT 20

(2) INFORMATION FOR SEQ ID NO:34:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:34:

AGACACTTAC AGATACCTAC AG 22

(2) INFORMATION FOR SEQ ID NO:35:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:35:

CACACCAGGC CCATATAAT 19

(2) INFORMATION FOR SEQ ID NO:36:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:36:

CCAAGGTACG GGAGGATC 18

(2) INFORMATION FOR SEQ ID NO:37:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:37:

GATCCTCCCG TACCTTG                                                                                    17

(2) INFORMATION FOR SEQ ID NO:38:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:38:

CACTGCAACA TCTGGTGAT                                                                                  19

(2) INFORMATION FOR SEQ ID NO:39:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:39:

TCACCAGATG TTGCAGTG                                                                                   18

(2) INFORMATION FOR SEQ ID NO:40:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:40:

GGCGTTGTTA CCTTAGCC                                                                                   18

(2) INFORMATION FOR SEQ ID NO:41:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:41:

GGCTAAGGTA ACAACGCC                                                                                   18

(2) INFORMATION FOR SEQ ID NO:42:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:42:

GGATACTACA CCTCCAG                                                                                    17

(2) INFORMATION FOR SEQ ID NO:43:

(i) SEQUENCE CHARACTERISTICS:

( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:43:

GCACAGGATT TTGTGTAGAG G	21

( 2 ) INFORMATION FOR SEQ ID NO:44:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:44:

TGTATTTGGC ACAGGATTTT G	21

( 2 ) INFORMATION FOR SEQ ID NO:45:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:45:

CAGGATTTTG TGTAGAGGCA	20

( 2 ) INFORMATION FOR SEQ ID NO:46:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:46:

CAAATCCTGT GCCAGGTAC	19

( 2 ) INFORMATION FOR SEQ ID NO:47:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:47:

GCACAGGATT TTGTGTAGAG	20

( 2 ) INFORMATION FOR SEQ ID NO:48:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:48:

TATTAGCACT GCCACTGCTG                                                           20

( 2 ) INFORMATION FOR SEQ ID NO:49:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:49:

CCCAACATTT ACTCCAAGTA AC                                                        22

( 2 ) INFORMATION FOR SEQ ID NO:50:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:50:

CTGAGGTTAG AAAGGAAAGC A                                                         21

( 2 ) INFORMATION FOR SEQ ID NO:51:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:51:

CACTTCTACT GCTATAACTT GT                                                        22

( 2 ) INFORMATION FOR SEQ ID NO:52:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:52:

ACACACCACC TAAAGGAAAG G                                                         21

( 2 ) INFORMATION FOR SEQ ID NO:53:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:53:

CGCAACCACA CAGTCTATGT                                                           20

( 2 ) INFORMATION FOR SEQ ID NO:54:

( i ) SEQUENCE CHARACTERISTICS:
 ( A ) LENGTH: 22 base pairs
 ( B ) TYPE: nucleic acid
 ( C ) STRANDEDNESS: single
 ( D ) TOPOLOGY: linear ( i i ) MOLECULE TYPE: DNA (genomic)

( x i ) SEQUENCE DESCRIPTION: SEQ ID NO:54:

TTCTACCTTA CTGGAAGACT GG    22

( 2 ) INFORMATION FOR SEQ ID NO:55:

( i ) SEQUENCE CHARACTERISTICS:
  ( A ) LENGTH: 19 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:55:

GGAGGTCAAT TTGCAAAAC    19

( 2 ) INFORMATION FOR SEQ ID NO:56:

( i ) SEQUENCE CHARACTERISTICS:
  ( A ) LENGTH: 19 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:56:

TGCAGGGGCA TTATTCTTT    19

( 2 ) INFORMATION FOR SEQ ID NO:57:

( i ) SEQUENCE CHARACTERISTICS:
  ( A ) LENGTH: 16 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:57:

TACAGCATCC ACGCAG    16

( 2 ) INFORMATION FOR SEQ ID NO:58:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:58:

CACGCAGGAT AGCTT    15

( 2 ) INFORMATION FOR SEQ ID NO:59:

( i ) SEQUENCE CHARACTERISTICS:
  ( A ) LENGTH: 16 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:59:

CCACGCAGGA TAGCTT 16

( 2 ) INFORMATION FOR SEQ ID NO:60:

( i ) SEQUENCE CHARACTERISTICS:
　　　　( A ) LENGTH: 20 base pairs
　　　　( B ) TYPE: nucleic acid
　　　　( C ) STRANDEDNESS: single
　　　　( D ) TOPOLOGY: linear ( i i ) MOLECULE TYPE: DNA (genomic)

( x i ) SEQUENCE DESCRIPTION: SEQ ID NO:60:

GTGCTGCTAC AACTCAGTCT 20

( 2 ) INFORMATION FOR SEQ ID NO:61:

( i ) SEQUENCE CHARACTERISTICS:
　　　　( A ) LENGTH: 20 base pairs
　　　　( B ) TYPE: nucleic acid
　　　　( C ) STRANDEDNESS: single
　　　　( D ) TOPOLOGY: linear ( i i ) MOLECULE TYPE: DNA (genomic)

( x i ) SEQUENCE DESCRIPTION: SEQ ID NO:61:

GCTACAACTC AGTCTCCATC 20

( 2 ) INFORMATION FOR SEQ ID NO:62:

( i ) SEQUENCE CHARACTERISTICS:
　　　　( A ) LENGTH: 17 base pairs
　　　　( B ) TYPE: nucleic acid
　　　　( C ) STRANDEDNESS: single
　　　　( D ) TOPOLOGY: linear ( i i ) MOLECULE TYPE: DNA (genomic)

( x i ) SEQUENCE DESCRIPTION: SEQ ID NO:62:

TGCCTTTTCA GGGGGAG 17

( 2 ) INFORMATION FOR SEQ ID NO:63:

( i ) SEQUENCE CHARACTERISTICS:
　　　　( A ) LENGTH: 20 base pairs
　　　　( B ) TYPE: nucleic acid
　　　　( C ) STRANDEDNESS: single
　　　　( D ) TOPOLOGY: linear ( i i ) MOLECULE TYPE: DNA (genomic)

( x i ) SEQUENCE DESCRIPTION: SEQ ID NO:63:

AATGTCTCTT TGTGTGCCAC 20

( 2 ) INFORMATION FOR SEQ ID NO:64:

( i ) SEQUENCE CHARACTERISTICS:
　　　　( A ) LENGTH: 19 base pairs
　　　　( B ) TYPE: nucleic acid
　　　　( C ) STRANDEDNESS: single
　　　　( D ) TOPOLOGY: linear ( i i ) MOLECULE TYPE: DNA (genomic)

( x i ) SEQUENCE DESCRIPTION: SEQ ID NO:64:

GTGTGCCACT GTAACCACA 19

( 2 ) INFORMATION FOR SEQ ID NO:65:

( i ) SEQUENCE CHARACTERISTICS:
 ( A ) LENGTH: 20 base pairs
 ( B ) TYPE: nucleic acid
 ( C ) STRANDEDNESS: single
 ( D ) TOPOLOGY: linear ( i i ) MOLECULE TYPE: DNA (genomic)

( x i ) SEQUENCE DESCRIPTION: SEQ ID NO:65:

GGATCAGTAG GGGTCTTAGG 20

( 2 ) INFORMATION FOR SEQ ID NO:66:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:66:

GCCAGTTAAA CAGGACCC 18

( 2 ) INFORMATION FOR SEQ ID NO:67:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:67:

CATAAGGGTC CTGTTTAACT G 21

( 2 ) INFORMATION FOR SEQ ID NO:68:

( i ) SEQUENCE CHARACTERISTICS:
  ( A ) LENGTH: 23 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:68:

ATTAATGCAG CTAAAAGCAC ATT 23

( 2 ) INFORMATION FOR SEQ ID NO:69:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:69:

GATGCCCGTG AAATCAATCA A 21

( 2 ) INFORMATION FOR SEQ ID NO:70:

( i ) SEQUENCE CHARACTERISTICS:
  ( A ) LENGTH: 19 base pairs
  ( B ) TYPE: nucleic acid
  ( C ) STRANDEDNESS: single
  ( D ) TOPOLOGY: linear (ii) MOLECULE TYPE: DNA (genomic)

(xi) SEQUENCE DESCRIPTION: SEQ ID NO:70:

TACTTGCAGT CTCGCGCCA                                                           19

(2) INFORMATION FOR SEQ ID NO:71:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:71:

CCAACACCGA ATCAGAATAT AAA                                                      23

(2) INFORMATION FOR SEQ ID NO:72:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:72:

GCACTGAAGT AACTAAGGAA GG                                                       22

(2) INFORMATION FOR SEQ ID NO:73:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:73:

AGCACCCCCT AAAGAAAAGG A                                                        21

(2) INFORMATION FOR SEQ ID NO:74:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:74:

GTAGGTACAC AGGCTAGTAG CTC                                                      23

(2) INFORMATION FOR SEQ ID NO:75:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:75:

GCTCTACTAC AACGTATGCC A                                                        21

( 2 ) INFORMATION FOR SEQ ID NO:76:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:76:

AGTTGCCAAC GTCCTCAAC                                                                 19

( 2 ) INFORMATION FOR SEQ ID NO:77:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:77:

GAGAT W TATK CATATGC                                                                 17

( 2 ) INFORMATION FOR SEQ ID NO:78:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:78:

GAGGTAT W TG AHTTTGC                                                                 17

( 2 ) INFORMATION FOR SEQ ID NO:79:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:79:

GTACTGCACG ACTATGT                                                                   17

( 2 ) INFORMATION FOR SEQ ID NO:80:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:80:

ACAAGACGTA TCTATTG                                                                   17

( 2 ) INFORMATION FOR SEQ ID NO:81:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear (ii) MOLECULE TYPE: DNA (genomic)

(xi) SEQUENCE DESCRIPTION: SEQ ID NO:81:

GCAAGACATA GAAATAA     17

(2) INFORMATION FOR SEQ ID NO:82:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:82:

ACCTTTGCAA CGATCTG     17

(2) INFORMATION FOR SEQ ID NO:83:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:83:

GAAGAGCCAA GGACAGGTAC     20

(2) INFORMATION FOR SEQ ID NO:84:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:84:

CAACTTCATC CACGTTCACC     20

(2) INFORMATION FOR SEQ ID NO:85:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:85:

ACACAACTGT GTTCACTAGC     20

DETECTION OF HUMAN PAPILLOMAVIRUS BY THE POLYMERASE CHAIN REACTION

This application is a continuation, of application Ser. No. 07/613,142, filed Nov. 14, 1990, now abandoned, which is a continuation-in-part (CIP) of PCT/US89/03747 filed Sep. 9, 1989, which issued as U.S. Pat. No. 5,283,171, which is a CIP of U.S. Ser. No. 322,550, filed Mar. 10, 1989, which issued as U.S. Pat. No. 5,182,377, which is a CIP of U.S. Ser. No. 243,486, filed Sep. 9, 1988, now abandoned, each of which is incorporated herein by reference.

BACKGROUND OF THE INVENTION

1. Field of the Invention

The present invention provides medical research and diagnostic methods for detecting and typing HPV. The methods utilize PCR, a DNA amplification technique widely used in the fields of molecular biology and genetic engineering. The methods can also be used to generate information concerning previously unknown types and sub-types of HPV and consequently has applications in the field of virology. 2. Description of Related Art Papillomaviruses have been linked to widespread, serious human diseases, especially carcinomas of the genital and oral mucosa. And although genital HPV infection is associated with cancer primarily in women, recent evidence suggests that HPV may play a role in the development of anogenital cancers in men. Broker et al., 1986, *Cancer Cells* 4:17-36, review the molecular, cellular, and clinical aspects of the papillomaviruses and the relationship of HPVs to cancer. HPV types 6, 11, 16, 18, and 33 are known genital HPV types in the human population, and Broker et al., 1986, *Cancer Cells* 4:589-594, disclose that HPV types 6, 11, 16, 18, and 33 share significant homology at the DNA level, particularly at the L1 open reading frame.

Identification and typing of HPV is quite important, because different types of HPV pose different risks to the affected individuals. For instance, HPV 16 and HPV 18 have been more consistently identified in higher grades of cervical dysplasia and carcinoma than other HPV types. Webb et al., December 1987, *J. Inf. Disease* 156(6):912-919, report a method for detecting HPV DNA types that utilizes a reverse-blotting procedure. The procedure involved forming a membrane to which genomic DNA from four different HPV types was bound and then hybridizing labelled DNA from a biological sample to the DNA bound to the membrane. Caussey et al., February 1988, *J. Clin. Microbiol.* 26(2):236-243 describe similar HPV detection methods.

Shibata et al., January 1988, *J. Exp. Med.* 167:225-230, disclose the use of PCR to amplify and detect the presence of HPV 16 and HPV 18 DNA. U.S. Pat. Nos. 4,683,195 and 4,683,202 disclose PCR and the use of PCR to detect the presence or absence of nucleic acid sequence in a sample. European Patent Publication Nos. 229,701 and 269,445 disclose the use of PCR to amplify and detect DNA sequences associated with a wide variety of viruses, including the AIDS virus, HTLV I, and HTLV II.

Maitland et al., May 1988, Seventh International Papillomavirus Workshop, Abstract, p. 5, report the use of PCR to detect HPV16 in oral and cervical biopsies. In addition, Campione-Piccardo et all., May 1988, Seventh International Papillomavirus Workshop, Abstract, p. 19, report the use of a mixture of primers for the specific amplification by PCR of HPV sequences in types 1a, 5, 6a, 6b, 8, 11, 16, 18, and 33. A number of other researchers disclosed the use of PCR to amplify and detect HPV sequences at the Seventh International Papillomavirus Workshop. Each of the background references described in this section is incorporated herein by reference.

The heterogeneity of the human papillomavirus group is generally described in deVilliers, 1989, *J. Virology* 63:4898-4903, which is incorporated herein by reference. The genomic of numerous HPV types have been sequenced and/or characterized. For example, for HPV type 6, see deVilliers et al., 1981, *J. Virology* 40:932-935, and Gissmann and Zur Hausen, 1980, *Int. J. Cancer* 25:605-609. For HPV type 2, see Gissmann et al., 1982, *J. Virology* 44:393-400. For HPV type 16, see Seedoff et al., 1985, *Virology* 145:181-185. For HPV type 18, see Cole and Danos, 1987, *J. Mol. Biol.* 193:599-608. For HPV type 31, see Goldsborough et al., 1989, *Virology* 171:306-311. For HPV 33, see Cole and Streeck, 1986, *J. Virology* 58:991-995. For HPV 54, see Favre et al., 1990, *Int. J. Cancer* 45:40-46. For HPV 56, see Lörinez, 1989, *J. Gen. Virol.* 70:3099. These publications are incorporated herein by reference.

Despite the use of PCR to amplify and detect HPV sequences, there still remains a need for a simple and rapid method for both detecting and typing HPV in a biological sample. The present invention provides a method that meets that need.

SUMMARY OF THE INVENTION

The present invention provides methods for detecting and typing HPV in a sample. The methods comprise amplifying a sequence of HPV DNA present in the sample, determining if amplification has occurred, and then hybridizing an HPV type-specific probe to the amplified DNA. The invention also provides novel primers and probes for use in the method. In a preferred embodiment long, generic probes are used for determining if amplification has occurred.

DETAILED DESCRIPTION

The present invention provides a method for detecting HPV in a sample, and typing the HPV if present, the method comprising:

(a) treating said sample with consensus HPV primers, an agent for polymerization, and deoxynucleoside 5'-triphosphates under hybridizing conditions, wherein said consensus HPV primers are mixtures of oligonucleotides that comprises at least a pair of primers sufficiently complementary to separate strands of the nucleic acid genome for each member of the group of HPV types that includes HPV-6, - 11, - 16, -18, and -33 to hybridize therewith, such that the extension product synthesized from one member of said pair, when separated from its complementary strand, can serve as a template for synthesis of the extension product of the other member of said pair;

(b) treating the sample under denaturing conditions to separate the primer extension products from their templates, providing single-stranded molecules;

(c) treating the products of step (b) with the consensus primers of step (a) under conditions such that a primer extension product is synthesized using each of the single-stranded molecules produced in step (b) as a template;

(d) repeating steps (b) and (c) to synthesize detectable amounts of said HPV nucleic acid, if present in said sample, providing an amplified HPV nucleic acid sequence;

(e) determining if amplification has occurred by treating the reaction mixture prepared in step (d) under hybridizing conditions with a long generic probe and determining if hybridization has occurred; and, if amplification has occurred, (f) hybridizing a type-specific DNA probe to said amplified DNA and determining if hybridization has occurred.

The first step in the method of the invention requires the use of consensus primer pairs that will amplify a discrete region of DNA from HPV DNA present in a sample. These consensus primer pairs are oligonucleotides, and the consensus primers may be mixtures of primer pairs. The mixtures used in the method assure that, regardless of the type of HPV present in a sample, HPV DNA corresponding to the region between the "consensus" sequences will be amplified. The PCR products generated from the consensus primers, if HPV is present in the sample, are then analyzed by hybridization with type-specific probes to determine the HPV types present.

Amplification of DNA by the polymerase chain reaction (PCR) is disclosed in U.S. Pat. Nos. 4,683,202 and 4,683,195 and incorporated herein by reference. PCR amplification of DNA involves repeated cycles of heat-denaturing the DNA, annealing two oligonucleotide primers to sequences that flank the DNA segment to be amplified, and extending the annealed primers with DNA polymerase. The primers hybridize to opposite strands of the target sequence and are oriented so DNA synthesis by the polymerase proceeds across the region between the primers, effectively doubling the amount of that DNA segment. Moreover, because the extension products are also complementary to and capable of binding primers, each successive cycle essentially doubles the amount of DNA synthesized in the previous cycle. This results in the exponential accumulation of the specific target fragment, at a rate of approximately $2^n$ per cycle, where n is the number of cycles.

The choice of primers for use in PCR determines the specificity of the amplification reaction. In the amplification steps of the method of the present invention, "consensus" primers are used that will amplify HPV sequences present in a sample, regardless of type. The consensus primers of the invention can include degenerate primers, mixtures of the oligonucleotides synthesized so that any one of several nucleotides can be incorporated into a primer at a selected position during synthesis. The consensus primers are sufficiently complementary to all types of HPVs to amplify a DNA sequence of any HPV present in the sample. The consensus primers are also designed to amplify a region of DNA that contains sequences that are specific to each major viral type, so the amplified DNA can therefore be used to type the HPV present in the sample. The consensus primers may also be suitable in a ligase chain reaction. For example, in PCT Patent Publication No. WO 89/09835, a process is described that involves the use of ligase to join oligonucleotide segments that anneal to the target nucleic acid. This publication is incorporated herein by reference.

The invention, although applicable to any HPV, is exemplified below with reference to genital and dermal HPV types. Furthermore, the primers and probes of the invention can be targeted to areas of the HPV genome other than those described below, provided that the particular area targeted can be amplified using consensus primers and the amplified DNA can be typed using type-specific probes.

The present invention has led and will continue to lead to the discovery of many previously unknown or uncharacterized HPV types. However, with each new HPV type discovered there comes a corresponding need to make the consensus probe more genetic to ensure that the new type will be detected and to make type-specific probes. To overcome this problem, the present invention provides an alternative type of consensus probe. This new type of probe, referred to herein as a long probe, comprises a sequence of DNA from one or more HPV viruses that comprises all or most of the HPV genomic DNA sequence that lies between two HPV amplification primers. Long probes provide enhanced sensitivity and reduce the likelihood of a false negative result even when a novel variant HPV-type is present.

The first step of the method of the present invention involves the amplification of an HPV sequence, if that sequence is present in a sample, by PCR using consensus primers. Illustrative consensus primers of the invention are referred to by the region of the HPV genome the primers are used to amplify. The HPV genome is circular. The genome of genital HPVs is oriented as follows: E6, E7, E1, E2, E4, E5a, E5b, L2, L1, and URR. "E" and "L" designations indicate open reading frames and URR indicates the transcriptional regulatory region. Several of the open reading frames overlap, for example, the E4 region is totally contained within the E2 open reading frame. Primers can be used to amplify a sequence that spans one or more regions of the HPV genome. The methods and compositions described herein are particularly suited for amplifying the following HPV regions: L1/URR, L1, E6, E6/E7, E7 through E1, E6 through E1, and E1. It will be clear to one of ordinary skill in the art that the methods disclosed are applicable to any region of the HPV genome and are not limited to the specific embodiments described herein. Throughout the specification nucleotides are designated as follows.

| Symbol | Meaning | Origin |
| --- | --- | --- |
| G | G | Guanine |
| A | A | Adenine |
| T | T | Thymine |
| C | C | Cytosine |
| R | G or A | puRine |
| Y | T or C | pYrimidine |
| M | A or C | aMino |
| K | G or T | Keto |
| S | G or C | Strong interaction (3 H bonds) |
| W | A or T | Weak interaction (2 H bonds) |
| H | A or C or T | not-G, H follows G in the alphabet |
| B | G or T or C | not-A, B follows A |
| V | G or C or A | not-T (not-U), V follows U |
| D | G or A or T | not-C, D follows C |
| N | G or A or T or C | aNy |

Following amplification, the method of the invention describes that a determination is made as to whether amplification has occurred. There are a variety of known means for determining whether amplification has occurred. For example, a portion of the PCR reaction mixture can be subjected to gel electrophoresis and the resulting gel stained with ethidium bromide and exposed to ultraviolet light to observe whether a product of the expected size is present. Alternatively, labeled PCR primers or deoxyribonucleoside 5'-triphosphates are utilized and incorporation of the label into the amplified DNA is determined by, for example, gel electrophoresis and autoradiograph to ascertain if amplification occurred. Another method for determining if amplification has occurred is to test a portion of PCR reaction mixture for ability to hybridize to a labeled probe designed to hybridize to only the amplified DNA. The probe must be a consensus probe so that amplified DNA from any HPV can be detected.

Alternatively, the determination of amplification and identification of HPV type can be carried out in one step by testing a portion of the PCR reaction mixture for its ability to hybridize to one or more type-specific probes. In another aspect of the invention multiple HPV infections are detected by restriction endonuclease digestion of amplification products. Restriction endonuclease analysis of amplified HPV DNAs is also useful for detecting variants and novel HPV types.

The invention encompasses consensus probes and type-specific probes. The probes may be oligonucleotides that are similar in length to primers or may be long probes. Long probes are especially preferred as the consensus probes for generic detection of amplified HPV nucleic acids.

As used herein "long probes" refer to nucleic acid segments used as generic probes for determining if amplification of any HPV has occurred. Long probes are generally greater than 100 nucleotides in length and may be as long as the amplified fragment they are designed to detect. Preferably, long probes are between 100-600 base pairs in length and comprise the full length of the amplified fragment to be detected, but do not include the primer sequences used to generate the amplified segment. For example, in Example II, the long probes are 410 nucleotides long (450, the L1 amplified product length-2×20, the L1 consensus primer length). The long probes are preferably PCR fragments. Most preferably, the PCR primers used to prepare the long probes are nested primers relative to the consensus primers used to amplify the HPV DNA in a sample so that the consensus primer sequences are not included in the probe.

The long probes are used as a mixture suitable for generic detection of HPV nucleic acids, and at least one nucleic acid in the generic long probe mixture will hybridize to each of HPV types -6, -11, -16, -18, and -33. However, it is not necessary to include amplified nucleic acids from each major HPV type in a long generic probe mixture. In one embodiment, Example I describes that long probes are prepared using HPV-16, HPV 18, and two clinical samples as the PCR template. The example describes a 410 base pair probe mixture that hybridizes to the major HPV types, as well as minor, variant, or novel HPV types. The long probes may be single-stranded or double-stranded. As used herein, long probes are also referred to as "generic probes" or "long generic probes."

Thus an important aspect of the present invention relates to the novel probes provided for use in the present methods. Whether these probes are consensus probes for determining if amplification has occurred or type-specific probes, the probes can be used in a variety of different hybridization formats. Although solution hybridization of a nucleic acid probe to a complementary target sequence is clearly within the scope of the present invention, commercialization of the invention will likely result in the use of immobilized probes and thus a quasi "solid-phase" hybridization. In this format, the probe is covalently attached to a solid support and then the target sequences are then hybridized to the probe. In this method, the probes are attached to a solid support by virtue of long stretches of T residues; these T residues are added to the probe during synthesis of the probe on an automated synthesizer after the hybridizing sequence is synthesized. When long probes are used in the method T-tailing is unnecessary and the probes can be attached directly to the solid support. A variety of dyes and chromogens and corresponding labels are available for nucleic acid detection systems.

In one embodiment, the L1/E6 consensus primer combinations of the invention are designed to amplify a sequence of DNA from any genital HPV. The amplified sequence extends from L1 across the URR and into E6 and thus contains portions of the L1 and E6 regions with the URR region sandwiched in between the L1 and E6 regions. Thus, the consensus primer pairs consist of a first primer specific for a sequence in the L1 region and a second primer specific for a sequence in the E6 region. As shown in Table 1, below, the first L1-specific primer can be either FS10, FS17, or MY01, while the second, E6-specific primer is at least a 1:1 mixture of JS15 and JS16, although the mixture can also contain more JS15 than JS16. Table 1 also depicts the sequence each primer and the corresponding sequence (and nucleotide position of that sequence) as it occurs in the genomes of several well-known genital HPVs (Types 6, 11, 16, 18, and 33). A dash in a sequence indicates that the genomic sequence is identical to the primer sequence.

TABLE 1

L1/E6 Consensus Primers and Amplification Products
L1 Consensus Positive Strand Primers

| | | | | | | | | | | | | | | | | | | | | | | | | | | |
|---|---|---|---|---|---|---|---|---|---|---|---|---|---|---|---|---|---|---|---|---|---|---|---|---|---|---|
| FS10 | 25mer | 5' | C | T | G | T | G | G | T | A | G | A | T | A | C | C | A | C | A | C | G | C | A | G | T | A | C |
| HPV06 | 6770 | | — | — | — | — | — | — | — | — | — | — | — | — | — | — | — | — | — | — | — | — | — | — | — | — |
| HPV11 | 6756 | | — | — | — | — | — | — | — | — | — | — | — | — | — | — | — | — | — | — | — | — | — | — | — | — |
| HPV16 | 6633 | | — | — | — | — | T | — | — | T | — | — | — | — | — | T | — | — | — | — | — | — | — | — | — | — |
| HPV18 | 6587 | | — | — | — | — | — | — | — | — | — | — | — | — | — | — | — | — | — | T | — | — | — | — | — | — |
| HPV33 | 6587 | | — | — | — | — | — | — | — | — | — | — | — | — | — | — | — | — | — | T | — | — | — | — | — | — |
| FS17 | 20mer | 5' | G | A | T | C | A | G | T | T | T | C | C | Y | Y | T | K | G | G | A | C | G | | | | |
| MY01 | 20mer | 5' | G | A | T | C | A | G | T | W | T | C | C | Y | Y | T | K | G | G | A | C | G | | | | |
| HPV06 | 7151 | | — | — | — | — | — | — | — | A | — | — | — | T | T | — | G | — | — | — | — | — | | | | |
| HPV11 | 7136 | | — | — | — | — | — | — | — | T | — | — | — | C | C | — | T | — | — | — | — | — | | | | |
| HPV16 | 7015 | | — | — | — | — | — | — | — | T | — | — | — | T | T | — | A | — | — | — | — | — | | | | |
| HPV18 | 6993 | | — | — | — | — | — | A | — | A | — | — | — | C | C | — | T | — | — | — | — | — | | | | |
| HPV33 | 6968 | | — | — | — | — | — | — | — | T | — | — | — | T | T | — | G | — | — | — | — | — | | | | |

URR/E6 Consensus Negative Strand Primer

| | | | | | | | | | | | | | | | | | | | |
|---|---|---|---|---|---|---|---|---|---|---|---|---|---|---|---|---|---|---|---|
| JS15 | 18mer | 5' | C | C G | T T | T T | C G | G T | T S | A A | C C | G | | | | | | | |

TABLE 1-continued

| | | | | | | | | | | | | | | | | | | | | | |
|---|---|---|---|---|---|---|---|---|---|---|---|---|---|---|---|---|---|---|---|---|---|
| HPV06 | 60 | | — | — — | — — | — — | — — | — — | — — | — — | — — | — G | — — | — | — — | | | | | | |
| HPV11 | 60 | | — | — — | — — | — — | — — | — — | — — | — — | — — | — G | — — | — | — — | | | | | | |
| HPV16 | 60 | | — | — — | G — | — — | — — | — — | — — | — — | — — | — C | — — | — | — — | | | | | | |
| HPV33 | 64 | | — | — — | — — | — — | — — | — — | — — | — — | — — | — G | — — | — | — — | | | | | | |
| JS16 | 19mer | 5' | C | C G | T T | T T | C G | G T | C | C C | G A | C | C G | | | | | | | | |
| HPV18 | 68 | | — | — — | — — | — — | — — | — — | — — | — — | — — | | | | | | | | | | | |

Predicted Sizes Of PCR Products

| + PRIMER | FS10 | FS17 or MYO1 |
|---|---|---|
| − PRIMER | JS15 and JS16 | JS15 and JS16 |
| HPV06 | 1192 bp | 822 bp |
| HPV11 | 1235 bp | 856 bp |
| HPV16 | 1387 bp | 958 bp |
| HPV18 | 1367 bp | 932 bp |
| HPV33 | 1434 bp | 1005 bp |

As shown in Table 1, FS 10 is a 25-mer that has 3 mismatches with HPV16 and 1 mismatch with HPV18 and HPV33. FS17 is a degenerate primer with 1 or 2 mismatches to different HPVs. MY01 is similar to FS 17, contains 1 more degenerate base to decrease mismatches and to potentially cover a wider range of HPVs. JS15 is a degenerate 18-mer for the negative strand in E6 of HPVs 6, 11, 16, and 33, whereas JS16 is a 19-mer serving the same function for HPV18.

Once a sample has been treated with the L1/E6 primers shown above under conditions suitable for PCR, the method of the invention requires the determination of whether amplification has occurred. If amplification has occurred with the L1/E6 primers, HPV sequences are present in the sample. In one aspect of the invention, a consensus probe is used to determine if amplification has occurred. Alternatively, amplification of HPV DNA using the L1/E6 consensus primers FS10, JS15, and JS16 can be detected using the L1/E6 consensus primer FS17 or MY01.

The present invention provides a number of type-specific probes for use with the L1/E6 consensus primers of the invention. These probes are set forth in Table 2, below. Those skilled in the art will recognize that although the specific primers and probes of the invention exemplified herein have a defined number of nucleotide residues, one or more nucleotide residues may be added or deleted from a given primer or probe typically without great impact on the suitability of that primer or probe in the present methods.

TABLE 2

HPV Typing Probes For Use with L1/E6 Consensus Primers

| Specificity | Sequence | Size | Designation |
|---|---|---|---|
| HPV6 | 5'CCAAACAGTAAGAGC | (15-mer) | FS18 |
| HPV11 | 5'GGCTGTAGAGGGCTTAGAC | (19-mer) | FS19 |
| HPV16 | 5'GGTTGAAGCTACAAAATGGGCC | (22-mer) | JS17 |
| HPV18 | 5'GTAGCGCACCTGGACAGG | (18-mer) | FS21 |
| HPV33 | 5'CAGGTAGTGACTCAC | (15-mer) | FS22 |

FS19 and JS17 can specifically detect HPV11 and HPV16, respectively. FS18 shows some hybridization with the HPV11 PCR product. UWGCG GAP program analysis comparing FS18 sequence and HPV11 sequence indicates a 73% homology of FS18 to HPV11 in the amplified region. The cross-hybridization could be minimized by increasing the stringency of washing. FS21 was specific for HPV18.

The L1/E6 primers disclosed above provide for the amplification of relatively large segments of HPV DNA. However, use of primers that result in shorter PCR products can have several advantages, including reduced extension and denaturation time and decreased denaturation temperature. The L1 consensus primers of the invention are illustrative of primers of the invention designed to amplify relatively small segments of the HPV genome to achieve such advantages. The L1 consensus primers produce a PCR product corresponding to sequences in the L1 open reading frame and are depicted in Table 3, below.

TABLE 3

L1 Consensus Primers and Amplification Products
L1 Consensus Positive Strand Primer

| | | | | | | | | | | | | | | | | | | | | | |
|---|---|---|---|---|---|---|---|---|---|---|---|---|---|---|---|---|---|---|---|---|---|
| MY11 | 20mer | 5' | G | C | M | C | A | G | G | G | W | C | A | T | A | A | Y | A | A | T | G G |
| HPV06 | 6722 | | — | — | C | — | — | — | — | A | — | — | — | — | — | C | — | — | — | — | — — |
| HPV11 | 6707 | | — | — | T | — | — | — | — | A | — | — | — | — | — | C | — | — | — | — | — — |
| HPV16 | 6584 | | — | — | A | — | — | — | — | C | — | — | C | — | — | C | — | — | — | — | — — |
| HPV18 | 6558 | | — | — | A | — | — | — | — | T | — | — | — | — | — | C | — | — | — | — | — — |
| HPV31 | | | — | — | T | — | — | — | — | A | — | — | C | — | — | T | — | — | — | — | — — |
| HPV33 | 6539 | | — | — | A | — | — | A | — | T | — | — | — | — | — | T | — | — | — | — | — — |

L1 Consensus Negative Strand Primer

| | | | | | | | | | | | | | | | | | | | | | |
|---|---|---|---|---|---|---|---|---|---|---|---|---|---|---|---|---|---|---|---|---|---|
| MY09 | 20mer | 5' | C | G | T | C | C | M | A | R | R | G | G | A | W | A | C | T | G | A | T C |
| HPV06 | 7171 | | — | — | — | — | — | C | — | A | A | — | — | — | T | — | — | — | — | — | A — |
| HPV11 | 7155 | | — | — | — | — | — | A | — | G | G | — | — | — | A | — | — | — | — | — | — — |
| HPV16 | 7035 | | — | — | — | — | — | T | — | A | A | — | — | — | A | — | — | — | — | — | — — |
| HPV18 | 7012 | | — | — | — | — | — | A | — | G | G | — | — | — | T | — | T | — | — | — | — — |
| HPV31 | | | — | — | A | — | — | C | — | A | A | — | — | — | A | — | — | — | — | — | — — |
| HPV33 | 6988 | | — | — | — | — | — | C | — | A | A | — | — | — | A | — | 1' | — | — | — | — — |
| HPV54 | | | — | — | A | — | — | A | — | — | G | — | — | — | A | — | — | — | — | G | — — |

TABLE 3-continued
Predicted sizes of PCR products from the MY11 and MY09 L1 Consensus Primer Pair HPV06 448 bp
HPV11 448 bp
HPV16 451 bp
HPV18 454 bp
HPV33 448 bp A preferred embodiment of the method of the present invention for genital HPVs comprises amplification of HPV sequences, if present in the sample, with the L1 consensus primers MY09 and MY11; determination of amplification by hybridization of a portion of the PCR reaction mixture with a generic HPV long probe; and finally, type determination with type-specific probes. The invention is useful for detecting any HPV DNA. In a preferred embodiment, which utilizes consensus primers MY09 and MY11, the method is useful for detecting and typing nucleic acids of both dermal and genital HPVs including genital HPV types 6, 6B, 11, 16, 18, 30, 31, 33, 35, 39, 40, 42, 43, 45, 51, 52, 53, 54, 55, 57, 58, and 59, as well as dermal HPV types 5, 8, 26, 27, 41, 47, and 48. At present, more than 60 unique HPV types have been identified. These are briefly described in deVilliers, 1989, *J. Virol.* 63:4898. The present invention is useful for typing known HPV types as well as identifying unique types or variants. To determine if amplification of HPV DNA sequences has occurred in a sample that has been treated with the L1 consensus primers of the invention, a portion of the PCR reaction mixture can be hybridized with L1 consensus probes, depicted in Table 4.

corresponding to the primers used in the amplification step of the present method. This diversity in HPV types also demonstrates the need for the type-specific probes provided by the present invention. In a preferred embodiment, the method utilizes a generic probe comprising PCR fragments. The PCR fragments provide long probes for the use as consensus probes for determining if amplification has occurred. According to Example 1, a generic probe was synthesized from the 450 base pair L1 PCR fragments of HPV-16, HPV-18, and the highly divergent isolates PAP88 and PAP238B. The generic probe described in Example 1 comprises segments approximately 400 base pairs in length and can be prepared using the primers depicted below. The primers are used in pairs corresponding to the target; i.e., MY74 (Seq ID No. 1) and MY75 (Seq ID No. 2) for HPV16, MY76 (Seq ID No. 3) and MY77 (Seq ID No. 4) for HPV18, MY47 (Seq ID No. 5) and MY48 (Seq ID No. 6) for PAP88, and MY49 (Seq ID No. 7) and MY50 (Seq ID No. 8) for PAP238B.

| Name | Internal PCR Primers for Generic Probe Sequence | Target |
|---|---|---|
| MY74 (SEQ ID NO. 1) | CATTTGTTGGGGTAACCAAC | HPV 16 |
| MY75 (SEQ ID NO. 2) | TAGGTCTGCAGAAAACTTTTC | HPV 16 |
| MY76 (SEQ ID NO. 3) | TGTTTGCTGGCATAATCAAT | HPV 18 |
| MY77 (SEQ ID NO. 4) | TAAGTCTAAAGAAAACTTTTC | HPV 18 |
| MY47 (SEQ ID NO. 5) | CATATGCTGGGGTAATCAGG | PAP 88 |
| MY48 (SEQ ID NO. 6) | CAGGTCTGCAGAAAAGCTGT | PAP 88 |
| MY49 (SEQ ID NO. 7) | TATTTGTTGGGGCAATCAG | PAP 238B |
| MY50 (SEQ ID NO. 8) | CTAAATCTGCAGAAAACTTTT | PAP 238B |

When a portion of the PCR reaction mixture contains DNA that hybridizes to a probe contained in the L1 consensus probe mixture, the sample contains HPV DNA. There are a number of ways to determine

TABLE 4
L1 Consensus Probes

| | | | | | | | | | | | | | | | | | | | | | | |
|---|---|---|---|---|---|---|---|---|---|---|---|---|---|---|---|---|---|---|---|---|---|---|
| FS10 | 5' | C | T | G | T | G | G | T | A | G | A | T | A | C | C | A | C | A | C | G | C | A | G | T | A | C |
| MY18 | 5' | — | — | — | — | T | — | — | T | — | — | — | — | — | T | — | — | — | — | — | — | — | — | — | — | — |
| MY19 | 5' | — | — | — | — | — | — | — | — | — | — | — | — | — | — | — | — | T | — | — | — | — | — | — | — | — |

Sequence of HPV types in Region of Consensus Probe

| | | | | | | | | | | | | | | | | | | | | | | | | | | | |
|---|---|---|---|---|---|---|---|---|---|---|---|---|---|---|---|---|---|---|---|---|---|---|---|---|---|---|---|
| HPV6 | 6771 | 5' | C | T | G | T | G | G | T | A | G | A | T | A | C | C | A | C | A | C | G | C | A | G | T | A | C |
| HPV11 | 6756 | 5' | — | — | — | — | — | — | — | — | — | — | — | — | — | — | — | — | — | — | — | — | — | — | — | — | — |
| HPV16 | 6631 | 5' | — | — | — | — | T | — | — | T | — | — | — | — | — | T | — | — | — | — | — | — | — | — | — | — | — |
| HPV18 | 6607 | 5' | — | — | — | — | — | — | — | — | — | — | — | — | — | — | — | — | T | — | — | — | — | — | — | — | — |
| HPV33 | 6588 | 5' | — | — | — | — | — | — | — | — | — | — | — | — | — | — | — | — | T | — | — | — | — | — | — | — | — |
| Isolate | 36 | 5' | — | — | — | — | T | — | — | G | — | — | — | — | — | T | — | — | — | C | A | — | A | — | — | C | — | — |
| Isolate | 88 | 5' | — | A | — | — | — | — | — | — | — | — | — | — | — | T | — | — | T | — | — | — | — | — | C | — | — |

As noted above, the diversity of HPV types may mandate the use of longer consensus probes that contain almost all of the amplified sequence except that portion whether a probe has hybridized to a DNA sequence contained in a sample. Typically, the probe is labeled in a detectable manner, the target DNA (i.e., the amplified DNA in the PCR reaction buffer) is bound to a solid support, and determination of whether hybridization has occurred simply involves determining whether the label is present on the solid support. This procedure can be varied, however, and is possible when the target is labeled and the probe is bound to the solid support.

Many methods for labelling nucleic acids, whether probe or target, are known in the art and are suitable for purposes of the present invention. Suitable labels may provide signals detectable by fluorescence, radioactivity, colorimetry, X-ray diffraction or absorption, magnetism, enzymatic activity, and the like. Suitable labels include fluoruphores, chromophores, radioactive isotopes (particularly $^{32}P$ and $^{125}I$), electrondense reagents, enzymes and ligands having specific binding partners. Enzymes are typically detected by their activity. For example, horse-radish-peroxidase (HRP) can be detected by its ability to convert diaminobenzidine to a blue pigment. A preferred method for HRP based detection uses tetramethyl-benzidine (TMB) as described in Clin. Chem. 33:1368 (1987). An alternative detection system is the Enhanced Chemiluminescent (ECL) detection kit commercially available from Amersham. The kit is used in accordance with the manufacturer's directions.

Probes are typically labeled with radioactive phosphorous $^{32}P$, by treating the probes with polynucleotide kinase in the presence of radiolabeled ATP. However, for commercial purposes non-radioactive labeling systems may be preferred, such as, horseradish peroxidase-avidin-biotin or alkaline phosphatase detection systems. HRP can be used in a number of ways. For example, if the primer or one or more of the dNTPs utilized in a PCR amplification has been labeled (for instance, the biotinylated dUTP derivatives described by Lo et al., 1988, Nuc. Acids Res. 16:8719) instead of the probe, then hybridization can be detected by assay for the presence of labeled PCR product. In a preferred embodiment, probes are biotinylated and detected with the ECL system described above. For example, biotinylated probes were prepared by direct biotinylation of the oligonucleotide rather than incorporation of biotin-dUTP during PCR. For 5' biotinylation of oligonucleotides direct solid phrase synthesis using biotin containing phosphoramidites was done according to Alves el al., 1989, Tetra. Let 30:3098; Cocuzza, 1989, Tetra Let. 30:6287; and Barabino et al., 1989, EMBO J. 8:4171. Solid phase synthesis of biotinylated oligonucleotides at any internal or terminal (5' or 3') position is also suitable for preparing biotinylated primers and probes (Pieles et al., 1989, NAR 18:4355, and Misiura et al., 1989, NAR 18:4345).

Alternatively, biotinylated probes can be prepared using terminal deoxynucleotide transferase (TdT) (Boeringer Mannheim) as follows. An 8:1 molar ratio of biotin-dUTP: oligonucleotide provided 80% derivatization with each molecule bearing 1 or more terminal biotin dUMPs. The tailing reaction contained 100 pmoles of oligonucleotide and 800 pmoles of biotin-dUTP in a 10–20 µl reaction using 3–10 units of TdT for 30–60 minutes at 37° C. The reaction buffer was prepared according to the enzyme specifications from the manufacturer. The reaction was stopped with EDTA and purified from 2.5 M NH$_4$Ac, by ethanol precipitation (twice) using 10 µg tRNA, ssDNA, glycogen or linearized acrylamide as a carder (see Focus 11(3):57–58). Tailed oligonuclcotides can be probes for targets fixed to a solid support. The Amersham ECL system provides an appropriate means for detecting these compounds (see Nature 346:297[1990]).

In one embodiment of the invention biotinylated probes are prepared by incorporating biotin-dUTP into the amplification reaction for preparing long probes.

Alternatively, probes are conjugated to HRP, for example, according to the method disclosed in WO 89/2932, and Beaucage et al., 1981, Tetra. Lett. 22:1859–1862. These references are incorporated herein by reference. For HRP conjugated probes, the hybridization buffer is adjusted to decrease the wash temperature required for removing non-specifically hybridized probe without the risk of denaturing the HRP enzyme. However, HRP conjugated probes are not used in the preferred embodiment. Whatever the labeling system used, once a determination has been made that the L1 consensus probe has hybridized to amplified DNA present in the sample, the amplified DNA is typed to determine the HPV types present in the sample.

Practice of the present invention has led to the discovery of many previously uncharacterized HPV types. For example, three clinical samples examined by the present method contained five different HPV types with sequences markedly different than the published sequences for HPVs. These new sequences are an important aspect of the present invention, as are the probes that will hybridize to these sequences in a type-specific fashion. These new sequences are depicted below. Degenerate nucleotides are as defined above and correspond to the degenerate nucleotides in the primers used to amplify the region or to variation within the type.

| The DNA Sequence of the L1 Amplified Regions of HPV Isolates 36A, 36B, 88, 238A, and 238B, 155, C14 | | | | | |
|---|---|---|---|---|---|
| | | Isolate 36A | | | |
| 1 | GCMCAGGGWC | ATAAYAATGG | TATATGTTGG | CACAATCAAT | TGTTTTTAAC |
| 51 | AGTTGTAGAT | ACTACTCGCA | GCACCAATCT | YTCTGTGTGT | GCTTCTACTA |
| 101 | CTTCTCCTAT | TCCTAATGAA | TACACACCTA | CCAGTTTTAA | AGAATATGCC |
| 151 | AGACATGTGG | RGGAATTTGA | TTTGCAGTTT | ATAYTTCAAC | TGTGTAAAAT |
| 201 | AACWTTAACT | ACAGAGGTAA | TGTCATACAT | TCATAATATG | AATACCACTA |
| 251 | TTTTGGAGGA | TTGGAATTTT | GGTRTTACAC | CACCTCCTAC | TGCTARTTTA |
| 301 | GTTGACACAT | ACCGTTTTGT | TCAATCTGCT | GCTGTAACTT | GTCAAAAGGA |
| 351 | CACCGCACCG | CCAGTTAAAC | AGGACCCTTA | TGACAAACTA | AAGTTTTGGA |
| 401 | CTGTAAATCT | TAAGGAAAGG | TTTTCTGCAG | ATCTTGATCA | GTWTCCYYTK |
| 451 | GGACG | | | | |
| | | Isolate 36B | | | |
| 1 | GCMCAGGGWC | ATAAYAATGG | TATATGTTGG | GGAAATCAGC | TATTTTTAAC |
| 51 | TGTGGTTGAT | ACTACCCGTA | GTACTAACAT | GACTTTGTGY | GCCACTGCAA |
| 101 | CATCTGGTGA | TACATATACA | GCTGCTAATT | TTAAGGAATA | TTTAAGACAT |
| 151 | GCTGAAGAAT | ATGATGTGCA | ATTTATATTT | CAATTGTGTR | AAATAACATT |
| 201 | AACTGTTGAA | GTTATGTCAT | ATATACACAA | TATGAATCCT | AACATATTAG |

The DNA Sequence of the L1 Amplified Regions of HPV Isolates 36A, 36B, 88, 238A, and 238B, 155, C14

-continued

| | | | | | |
|---|---|---|---|---|---|
| 251 | AGGAGTGGAA | TGTTGGTGTT | GCACCACCAC | CTTCAGGAAC | TTTAGAAGAT |
| 301 | AGTTATAGGT | ATGTACAATC | AGAAGCTATT | CGCTGTCAGG | CTAAGGTAAC |
| 351 | AACGCCAGAA | AAAAAGGATC | CTTATTCAGA | CTTTTCCTTT | TGGGAGGTAA |
| 401 | ATTTATCTGA | AAAGTTTTCT | ACTGATTTAG | GATCAGTWTC | CYYTKGGACG |

Isolate 88

| | | | | | |
|---|---|---|---|---|---|
| 1 | GCMCAGGGWC | ATAAYAATGG | CATATGCTGG | GGTAATCAGG | TATTTGTTAC |
| 51 | TGTTGTGGAT | ACTACCAGAA | GCACCAACAT | GACTATTAAT | GCAGCTAAAA |
| 101 | GCACATTARC | TAAATATGAT | GCCCGTGAAA | TCAATCAATA | CCTTCGCCAT |
| 151 | GTGGAGGAAT | ATGAACTACA | GTTTGTGTTT | CAACTTTGTA | AAATAACCTT |
| 201 | AACTGCAGAR | GTTATGGCAT | ATTTGCATAA | TATGAATAAT | ACTTTATTRG |
| 251 | ACGATTGGAA | TATTGGCTTA | TCCCCACCAG | TTGCAACTAG | CTTAGAGGAT |
| 301 | AAATATAGGT | ATATTAAAAG | CACAGCTRTT | ACAYGTCAGA | GGGAACAGCC |
| 351 | CCCTGCAGAA | AAGCAGGATC | CCCTGGCTAA | ATATAAGTTT | TGGGAAGTTA |
| 401 | ATTTACAGGA | CAGCTTTTCT | GCAGACCTGG | GATCAGTWTC | CYYTKGGACG |

Isolate 238A

| | | | | | |
|---|---|---|---|---|---|
| 1 | GCMCAGGGWC | ATAAYAATGG | TATTTGTTGG | VATAATCART | TATTTTTAAC |
| 51 | TGTTGTAGAT | ACTACTAGAA | GCACTAATTT | TTCTGTATGT | GTAGGTACAC |
| 101 | AGGCTAGTAG | CTCTACTACA | ACGTATGCCA | ACTCTAATTT | TAAGGAATAT |
| 151 | TTAAGACATG | CAGAAGAGTT | TGATTTACAG | TTTGTTYTTC | AGTTATGTAA |
| 201 | AATTAGTTTA | ACTACTGAGG | TAATGACATA | TATACATTCT | ATGAATTCTA |
| 251 | CTATATTGGA | AGAGTGGAAT | TTTGGTCTTA | CCCCACCACC | GTCAGGTACT |
| 301 | TTAGAGGAAA | CATATAGATA | TGTAACATCA | CAKGCTATTA | GTTGCCAACG |
| 351 | TCCTCAACCT | CCTAAAGAAA | CAGAGGACCC | ATATGCCAAG | CTATCCTTTT |
| 401 | GGGATGTAGA | TCTTAAGGAA | AAGTTTTCTG | CAGAATTAGA | TCAGTWTCCY |
| 451 | YTKGGACG | | | | |

Isolate 238B

| | | | | | |
|---|---|---|---|---|---|
| 1 | GCMCAGGGWC | ATAAYAATGG | TATTTGTTGG | GGCAATCAGT | TATTTGTTAC |
| 51 | TGTGGTAGAT | ACCACACGTA | GTACCAATAT | GTCTGTGTGT | GCTGCAATTG |
| 101 | CAAACAGTGA | TACTACATTT | AAAAGTAGTA | ATTTTAAAGA | GTATTTAAGA |
| 151 | CATGGTGAGG | AATTTGATTT | ACRATTTATA | TTTCAGTTAT | GCAAAATAAC |
| 201 | ATTATCTGCA | GACATAATGA | CATATATTCA | CAGTATGAAT | CCTGCTATTT |
| 251 | TGGAAGATTG | GAATTTTGGA | TTGACCACAC | CTCCCTCAGG | TTCTTTAGAG |
| 301 | GATACCTATA | GGTTTGTAAC | CTCACAGGCC | ATTACATGTC | AAAAARCTGC |
| 351 | CCCCCAAAAG | CCCAAGGAAG | ATCCATTTAA | AGATTATGTA | TTTTGGGAGG |
| 401 | TTAATTTAAA | AGAAAAGTTT | TCTGCAGATT | TAGATCAGTW | TCCYYTKGGA |
| 451 | CG | | | | |

Isolate 155A and 155B

| | | | | | |
|---|---|---|---|---|---|
| 1 | TATATGCTGG | TTTAATCAAT | TGTTTGTCAC | GGTGGTGGAT | ACCACCCGCA |
| 51 | GCACCAATTT | TACTATTAGT | GCTGCTACCA | ACACCGAATC | AGAATATAAA |
| 101 | CCTACCAATT | TTAAGGAATA | CCTAAGACAT | GTGGAGGAAT | ATGATTTGCA |
| 151 | GTTTATATTC | CAGTTGTGTA | AGGTCCGTCT | GACTCCAGAG | GTCATGTCCT |
| 201 | ATTTACATAC | TATGAATGAC | TCCTTATTAG | ATGAGTGGAA | TTTTGGTGTT |
| 251 | GTGCCCCCTC | CCTCCACAAG | TTTAGATGAT | ACCTATAGGT | ACTTGCAGTC |
| 301 | TCGCGCCATT | ACTTGCCAAA | AGGGGGCCGC | CGCCGCCAAG | CCTAAGGAAG |
| 351 | ATCCTTATGC | TGGCATGTCC | TTTTGGGATG | TAGATTTAAA | GGACAAGTTT |
| 401 | TCTACTGATT | TG | | | |

Isolate C14

| | | | | | |
|---|---|---|---|---|---|
| 1 | TATTTGTTGG | CATAATCAGT | TGTTTGTTAC | TGTAGTGGAC | ACTACCCGCA |
| 51 | GTACTAATTT | AACATTATGT | GCCCTCTACAC | AAAATCCTGT | GCCAAATACA |
| 101 | TATGATCCTA | CTAAGTTTAA | GCACTATAGT | AGACATGTGG | AGGAATATGA |
| 151 | TTTACAGTTT | ATTTTTCAGT | TGTGCACTAT | TACTTTAACT | GCAGAGGTTA |
| 201 | TGCCATATAT | CCATAGTATG | AATAGTAGTA | TATTGGAAAA | TTGGAATTTT |
| 251 | GGTGTACCTC | CACCACCTAC | TACAAGTTTA | GTGGATACAT | ATCGTTTTGT |
| 301 | GCAATCCGTT | GCTGTTACCT | GTCAAAAGGA | TACTACACCT | CCAGAAAAGC |
| 351 | AGGATCCATA | TGATAAATTA | AAGTTTTGGA | CTGTTGACCT | AAAGGAAAAA |
| 401 | TTTTCCTCCG | ATTTG | | | |

Those skilled in the art will recognize that with the above sequence information, primers and probes for amplifying and detecting these new HPV isolates can be readily obtained. In addition, these sequences enable one to isolate the entire virus from samples containing the virus. Isolate 36A is an HPV59 variant, and isolate 36B is an HPV42 variant. Isolate 238B corresponds to the HPV31 type described in the literature. A cervical carcinoma isolate, C14, is a variant of HPV45. The discovery of these new HPV isolates led to the creation of additional L1 consensus oligonucleotide probes for use in conjunction with FS10, MY18, and MY19. These L1 consensus probes are depicted below under the FS 10 probe sequence to demonstrate the similarity to the FS10 sequence. L1 consensus probe WD147 will hybridize to HPV45 DNA. MY46 (Seq ID No. 9) is a combination of FS10 and MY19. In one embodiment, a consensus L1 probe can be an equimolar mixture of MY 18, MY46, (Seq ID No. 9) MY57, and WD 147.

| | | | | | | | | | | | | | | | | | | | | | | |
|---|---|---|---|---|---|---|---|---|---|---|---|---|---|---|---|---|---|---|---|---|---|---|
| FS10 | 5' | C | T | G | T | G | G | T | A | G | A | T | A | C | C | A | C | A | C | G | C | A | G | T | A | C |
| MY66 |  | — | A | — | — | T | — | — | — | — | — | — | — | — | — | T | — | — | T | — | — | — | — | — | C | — | — |
| MY55 |  | — | — | — | — | — | — | — | T | — | — | — | — | — | T | — | — | C | — | — | T | — | — | — | — | — | — |
| MY39 |  | — | — | — | — | T | — | — | G | — | — | — | — | — | T | — | — | C | A | — | A | — | — | — | C | — | — |
| MY56 |  | — | — | — | — | T | — | — | — | — | — | — | — | — | T | — | — | T | A | — | A | — | — | — | C | — | — |
| MY57 |  | — | — | — | — | — | — | — | — | — | — | — | — | — | — | — | — | — | — | — | T | — | — | — | — | — | — |
| WD147 |  | — | — | — | — | A | — | — | G | — | — | C | — | — | T | — | — | C | — | — | — | — | — | — | — | — | — |

| | | | | | | |
|---|---|---|---|---|---|---|
| MY46 (SEQ ID NO. 9) | — — — | — — — — | — — — | — — — — | W — — — — | — — — |

The present invention provides a number of probes for typing amplified DNA produced from L1 consensus primers. While most probes for typing HPV hybridize to known HPV types, others specifically detect previously uncharacterized HPV types and hybridize to novel HPVs identified in clinical samples as a result of use of the present methods. These probes are depicted below in Table 5.

TABLE 5

HPV Typing Probes For Use with L1 Consensus Primers

| Probe | Specificity | Sense | Sequence | Genome 5' Position | Biotinylated Versions |
|---|---|---|---|---|---|
| MY12 | HPV6 | + | CATCCGTAACTACATCTTCCA | 6813 | MY134 |
| MY62 | HPV6 | + | CTCCTGAAAAGGAAAAGCCA | 7068 | |
| MY63 | HPV6 | − | TGGCTTTTCCTTTTCAGGAG | 7068 | MY135 |
| MY125 (SEQ ID NO. 10) | HPV6/HPV11 | + | ACAATGAATCYTCTGTTTTGG | 6950/6935 | MY138 |
| MY126 (SEQ ID NO. 11) | HPV6/HPV11 | + | ATCGCCTCCMCCAAATG | 6991/6976 | |
| MY13 | HPV11 | + | TCTGTGTCTAAATCTGCTACA | 6800 | MY136 |
| MY61 | HPV11 | + | CACACCTGAAAAAGAAAAACAG | 7051 | |
| MY65 | HPV11 | − | CTGTTTTTCTTTTTCAGGTGTG | 7051 | MY137 |
| WD150 | HPV11 | + | CAGAAACCCACACCTGAAAAAGA | 7059 | |
| WD151 | HPV11 | + | AGAAACCCACACCTGAAAAAGAA | 7058 | |
| MY14 | HPV16 | + | CATACACCTCCAGCACCTAA | 6926 | MY14 |
| MY58 | HPV16 | + | TTGTAACCCAGGCAATTGCT | 6897 | |
| MY71 (SEQ ID NO. 12) | HPV16 | + | ACATACACCTCCAGCACCTA | 6925 | |
| MY72 (SEQ ID NO. 13) | HPV16 | + | CATACACCTCCAGCACCTA | 6926 | |
| MY95 (SEQ ID NO. 14) | HPV16 | − | GATATGGCAGCACATAATGAC | 6685 | MY139 |
| MY96 (SEQ ID NO. 15) | HPV16 | − | AGTTTCTGAAGTAGATATGGCA | 6698 | |
| MY97 (SEQ ID NO. 16) | HPV16 | − | CTGAAGTAGATATGGCAGCAC | 6693 | |
| MY133 (SEQ ID NO. 17) | HPV16 | + | GTAACATCCCAGGCAATTG | 6897 | MY140 |
| WD152 | HPV16 | + | TTTGTAACCCAGGCAATTGCT | 6898 | |
| WD153 | HPV16 | + | GTTGTAACCCAGGCAATTGCT | 6897 | |
| MY60 | HPV18 | + | CAGTCTCCTGTACCTGGG | 6657 | |
| MY73 (SEQ ID NO. 18) | HPV18 | + | GATGCTGCACCGGCTGAA | 6906 | |
| MY107 (SEQ ID NO. 19) | HPV18 | − | GCCCAGGTACAGGAGAC | 6659 | |
| MY130 (SEQ ID NO. 20) | HPV18 | + | GGGCAATATGATGCTACCAAT | 6672 | MY142 |
| MY131 (SEQ ID NO. 21) | HPV18 | + | GTACCTGGGCAATATGATG | 6666 | |
| MY132 (SEQ ID NO. 22) | HPV18 | + | TCTCCTGTACCTGGGCAA | 6660 | |
| WD74 | HPV18 | + | GGATGCTGCACCGGCTGA | 6905 | MY141 |
| WD75 (SEQ ID NO. 23) | HPV18 | − | TCAGCCGGTGCAGCATCC | 6922 | |
| WD126 | HPV31 | + | CCAAAAGCCCAAGGAAGATC | 6851 | |
| WD127 | HPV31 | + | CAAAAGCCCAAGGAAGATC | 6852 | |
| WD128 | HPV31 | + | TTGCAAACAGTGATACTACATT | 6597 | MY143 |
| MY109 (SEQ ID NO. 24) | HPV31 | − | GAGGGAGGTGTGGTCAAT | 6769 | |
| MY110 (SEQ ID NO. 25) | HPV31 | − | AAGAACCTGAGGGAGGT | 6778 | |
| MY92 (SEQ ID NO. 26) | HPV31/HPV31B | + | CCAAAAGCCYAAGGAAGATC | 6853 | MY144 |
| MY127 (SEQ ID NO. 27) | HPV31/HPV31B | + | ACCACACCTCCCTCAG | 6773 | |
| MY128 (SEQ ID NO. 28) | HPV31/HPV31B | + | ACAGGCCATTACATGTCAA | 6823 | |
| MY16 | HPV33 | + | CACACAAGTAACTAGTGACAG | 6628 | MY145 |
| MY59 | HPV33 | + | AAAAACAGTACCTCCAAAGGA | 6877 | |
| MY64 | HPV33 | − | TCCTTTGGAGGTACTGTTTTT | 6877 | MY146 |
| MY115 (SEQ ID NO. 29) | HPV35 | + | CTGCTGTGTCTTCTAGTGACAG | | |
| MY116 (SEQ ID NO. 30) | HPV35 | + | TGCACCAAAACCTAAAGATG | | |
| MY117 (SEQ ID NO. 31) | HPV35 | − | ATCATCTTTAGGTTTTGGTGC | | |
| MY89 (SEQ ID NO. 32) | HPV39 | + | TAGAGTCTTCCATACCTTCTAC | | MY147 |
| MY90 (SEQ ID NO. 33) | HPV39 | + | CTGTAGCTCCTCCACCATCT | | MY148 |

TABLE 5-continued
HPV Typing Probes For Use with L1 Consensus Primers

| Probe | Specificity | Sense | Sequence | Genome 5' Position | Biotinylated Versions |
|---|---|---|---|---|---|
| MY91 (SEQ ID NO. 34) | HPV39 | + | AGACACTTACAGATACCTACAG | | |
| MY118 (SEQ ID NO. 35) | HPV40 | + | CACACCAGGCCCATATAAT | | |
| MY119 (SEQ ID NO. 36) | HPV40 | + | CCAAGGTACGGGAGGATC | | |
| MY120 (SEQ ID NO. 37) | HPV40 | − | GATCCTCCCGTACCTTG | | |
| MY121 (SEQ ID NO. 38) | HPV42 | + | CACTGCAACATCTGGTGAT | | |
| MY122 (SEQ ID NO. 39) | HPV42 | − | TCACCAGATGTTGCAGTG | | |
| MY33 (SEQ ID NO. 40) | HPV42 | − | GGCGTTGTTACCTTAGCC | | |
| MY34 (SEQ ID NO. 41) | HPV42 | + | GGCTAAGGTAACAACGCC | | |
| MY68 (SEQ ID NO. 42) | HPV45 | + | GGATACTACACCTCCAG | | |
| MY69 | HPV45 | + | ATACTACACCTCCAGAAAAGC | | MY149 |
| MY70 | HPV45 | + | TAGTGGACACTACCCGCAG | | |
| MY98 (SEQ) | HPV45 | − | GCACAGGATTTTGTGTAGAGG | | |
| MY99 (SEQ ID NO. 43) | HPV45 | − | TGTATTTGGCACAGGATTTTG | | |
| MY100 (SEQ ID NO. 44) | HPV45 | − | CAGGATTTTGTGTAGAGGCA | | |
| MY108 (SEQ ID NO. 45) | HPV45 | + | CAAATCCTGTGCCAGGTAC | | |
| MY129 (SEQ ID NO. 46) | HPV45 | − | GCACAGGATTTTGTGTAGAG | | MY150 |
| MY87 (SEQ ID NO. 47) | HPV51 | + | TATTAGCACTGCCACTGCTG | | |
| MY88 (SEQ ID NO. 48) | HPV51 | + | CCCAACATTTACTCCAAGTAAC | | |
| MY80 (SEQ ID NO. 49) | HPV52 | + | CTGAGGTTAGAAAGGAAAGCA | | |
| MY81 (SEQ ID NO. 50) | HPV52 | + | CACTTCTACTGCTATAACTTGT | | |
| MY82 (SEQ ID NO. 51) | HPV52 | + | ACACACCACCTAAAGGAAAGG | | |
| MY101 (SEQ ID NO. 52) | HPV53 | + | CGCAACCACACAGTCTATGT | | |
| MY102 (SEQ ID NO. 53) | HPV53 | + | TTCTACCTTACTGGAAGACTGG | | |
| MY103 (SEQ ID NO. 54) | HPV53 | + | GGAGGTCAATTTGCAAAAC | | |
| MY111 (SEQ ID NO. 55) | HPV54 | − | TGCAGGGGCATTATTCTTT | | |
| MY112 (SEQ ID NO. 56) | HPV54 | + | TACAGCATCCACGCAG | | |
| MY113 (SEQ ID NO. 57) | HPV54 | + | CACGCAGGATAGCTT | | |
| MY114 (SEQ ID NO. 58) | HPV54 | + | CCACGCAGGATAGCTT | | |
| MY151 (SEQ ID NO. 59) | HPV55 | + | GTGCTGCTACAACTCAGTCT | | |
| MY152 (SEQ ID NO. 60) | HPV55 | + | GCTACAACTCAGTCTCCATC | | |
| MY153 (SEQ ID NO. 61) | HPV55 | − | TGCCTTTTCAGGGGGAG | | |
| MY154 (SEQ ID NO. 62) | HPV57 | + | AATGTCTCTTTGTGTGCCAC | | |
| MY155 (SEQ ID NO. 63) | HPV57 | + | GTGTGCCACTGTAACCACA | | |
| MY156 (SEQ ID NO. 64) | HPV57 | − | GGATCAGTAGGGGTCTTAGG | | |
| MY123 (SEQ ID NO. 65) | HPV59 | + | GCCAGTTAAACAGGACCC | | |
| MY124 (SEQ ID NO. 66) | HPV59 | − | CATAAGGGTCCTGTTTTAACTG | | |
| MY83 (SEQ ID NO. 67) | PAP88 | + | ATTAATGCAGCTAAAAGCACATT | | |
| MY84 (SEQ ID NO. 68) | PAP88 | + | GATGCCCGTGAAATCAATCAA | | |
| MY86 (SEQ ID NO. 69) | PAP155 | + | TACTTGCAGTCTCGCGCCA | | |
| MY85 (SEQ ID NO. 70) | PAP155 | + | CCAACACCGAATCAGAATATAAA | | |
| MY93 (SEQ ID NO. 71) | PAP251 | + | GCACTGAAGTAACTAAGGAAGG | | |

TABLE 5-continued

HPV Typing Probes For Use with L1 Consensus Primers

| Probe | Specificity | Sense | Sequence | Genome 5' Position | Biotinylated Versions |
|---|---|---|---|---|---|
| ID NO. 72) | | | | | |
| MY94 (SEQ ID NO. 73) | PAP251 | + | AGCACCCCCTAAAGAAAAGGA | | |
| MY104 (SEQ ID NO. 74) | PAP238A | + | GTAGGTACACAGGCTAGTAGCTC | | |
| MY105 (SEQ ID NO. 75) | PAP238A | + | GCTCTACTACAACGTATGCCA | | |
| MY106 (SEQ ID NO. 76) | PAP238A | + | AGTTGCCAACGTCCTCAAC | | |

The present invention also provides consensus primers and HPV typing probes for detection of DNA sequences specific for the E6 region of genital HPVs. These probes are particularly preferred, because in some cancers, the HPV genome is partially deleted or rearranged such that only E6- and E7-related sequences are present. The E6 consensus primer pairs of the invention comprise primer pairs in which one primer is complementary to sequences near the border of the URR and E6 regions and the other primer is complementary to sequences in either the E7 region near the E6-E7 border (the E6 and E7 open reading frames overlap) or in the E6 region. These E6 consensus primers are depicted below in Table 6.

Although E6 consensus primers, consensus probes, and type specific probes are suitable for detecting and typing HPV nucleic acids, they also have utility when used in conjunction with L1 primers and probes. In one embodiment of the invention, the E6 gene was chosen as a site for a second consensus primer set and type specific probes. The use of E6 as a second site for detection and typing may allow detection of such integrated HPVs. The smaller E6 PCR products also increase the likelihood of detecting HPV sequences in archival tissues where DNA may be too fragmented to serve as a template for long PCR products.

While it is not an essential aspect of the present invention, the use of two sites allows rapid confirmation of typing results, thereby increasing the confidence level of the data. The use of a second site also circumvents the prospect of false negativity as a consequence of sequence variation in one of the primer binding sites.

TABLE 6

E6 Consensus Primers
URR/E6 Consensus Positive Strand Primers

| WD73 |     | 5' | C | G | G | T |   | T | S | A |   | A | C | C | G | A | A | A | A | C |   | G | G |
|---|---|---|---|---|---|---|---|---|---|---|---|---|---|---|---|---|---|---|---|---|---|---|---|
| WD72 |     | 5' | C | G | G | T |   | C | G | G | G | A | C | C | G | A | A | A | A | C |   | G | G |
| WD76 |     | 5' | C | G | G | T |   | T | S | A |   | A | C | C | G | A | A | A | M | C |   | G | G |
| WD77 |     | 5' | C | G | G | T |   | T | C | A |   | A | C | C | G | A | A | A | M | C |   | G | G |
| HPV6 | 43 | 5' | C | G | G | T |   | T | C | A |   | A | C | C | G | A | A | A | A | C |   | G | G |
| HPV11 | 43 | — | — | — | — |   | — | — | — |   | — | — | — | — | — | — | — | — | — |   | — | — |
| HPV16 | 43 | — | — | — | — |   | — | G | — |   | — | — | — | — | — | — | — | C | — |   | — | — |
| HPV18 | 43 | — | — | — | — |   | C | G | G | G | — | — | — | — | — | — | — | — | — |   | — | — |
| HPV31 | 45 | G | T | — | G |   | — | G | — |   | — | — | — | — | — | — | — | — | — |   | — | — |
| HPV33 | 65 | — | — | — | — |   | — | — | — |   | — | — | — | — | — | — | — | — | — |   | — | — |

The URR/E6 positive strand primers are used as mixtures: WD72 and WD73; WD72 and WD76; and WD72 and WD77.

E7 Consensus Negative Strand Primer

| WD70 |     | 5' | G | C | R | C | A | G | A | T | G | G | G | R | C | A | C | A | C |   |   |   |   |
| --- | --- | --- | --- | --- | --- | --- | --- | --- | --- | --- | --- | --- | --- | --- | --- | --- | --- | --- | --- | --- | --- | --- | --- |
| WD71 |     | 5' | G | C | A | C | A | C | C | A | C | G | G | A | C | A | C | A | C |   |   |   |   |
| HPV06 | 813 | 5' | G | C | G | C | A | G | A | T | G | G | G | A | C | A | C | A | C |   |   |   |   |
| HPV11 | 813 | — | — | — | — | — | — | — | — | — | — | — | — | — | — | — | — | — |   |   |   |   |
| HPV16 | 845 | — | A | A | — | — | — | — | — | — | — | — | G | — | — | — | — | — |   |   |   |   |
| HPV18 | 894 | — | — | A | — | — | — | C | C | A | C | — | — | — | — | — | — | — |   |   |   |   |
| HPV33 | 856 | — | — | A | — | — | — | G | — | A | — | — | G | — | — | — | — | — |   |   |   |   |
| WD68 |     | 5' | C | A | C | A | C | A | A | T | D | Y | Y | Y | A | G | T | G | T | G | C | C | C |
| WD69 |     | 5' | C | A | C | A | C | A | A | A | G | G | A | C | A | G | G | G | T | G | T | T | C |
| HPV06 | 801 | 5' | C | A | C | A | C | T | A | T | G | T | T | T | A | G | T | G | T | T | C | C | C |
| HPV11 | 801 | — | — | — | — | — | A | — | — | A | — | — | — | — | — | — | — | — | G | — | — | — |
| HPV16 | 833 | — | — | — | — | — | A | — | — | T | C | C | — | — | — | — | — | — | G | — | — | — |
| HPV18 | 882 | — | — | — | — | — | A | — | A | — | G | A | C | — | — | G | — | G | T | T | — |   |
| HPV33 | 844 | — | — | — | — | — | A | — | — | A | — | — | C | — | C | — | — | — | G | — | — | — |

The E7 negative strand primers are used as mixtures: WD70 and WD71; and WD68 and WD69.

E6 Consensus Negative Strand Primer

| WD67 |     | W | G | C | A | W | A | T | G | G | A | W | W | G | C | Y | G | T | C | T | C |
|---|---|---|---|---|---|---|---|---|---|---|---|---|---|---|---|---|---|---|---|---|---|
| WD66 |     | A | G | C | A | T | G | C | G | G | T | A | T | A | C | T | G | T | C | T | C |
| WD154 |     | T | C | C | G | T | G | T | G | G | T | G | T | G | T | C | G | T | C | C | C |
| WD155 |     | W | S | C | A | W | A | T | G | G | W | W | W | G | Y | C | G | T | C | Y | C |
| WD163 |     | W | G | C | A | W | A | T | G | G | A | W | W | G | Y | Y | G | T | C | Y | C |
| WD164 |     | W | S | C | A | W | A | T | G | G | W | D | W | G | Y | Y | G | T | C | Y | C |
| HPV6 | 286 | T | G | C | A | T | A | T | G | G | A | T | A | G | C | C | G | C | C | T | C |
| HPV11 | 286 | — | — | — | — | A | — | G | — | — | — | A | — | — | T | T | — | T | — | — | — |
| HPV16 | 286 | A | — | — | — | — | — | — | — | — | — | T | T | — | — | — | A | T | — | — | — |
| HPV18 | 292 | A | — | — | — | — | G | C | — | — | T | A | T | A | — | T | — | T | — | — | — |
| HPV31 |     | — | C | — | G | — | G | — | — | — | T | G | T | — | T | — | — | T | — | C | — |
| HPV33 | 390 | — | C | — | — | A | — | — | — | — | — | — | T | — | — | — | C | T | — | — | — |
| HPV43 |     | A | — | — | A | A | — | C | — | — | — | — | — | T | — | — | — | T | — | G | — |

TABLE 6-continued

| | | | | | | | | | | | | | | | | | | | |
|---|---|---|---|---|---|---|---|---|---|---|---|---|---|---|---|---|---|---|---|
| HPV44 | — | — | — | — | A | — | T | — | — | — | A | — | — | T | T | T | — | — | — | — |
| HPV56 | — | — | — | — | — | A | — | — | — | — | A | — | A | T | — | A | T | — | C | — |

The E6 negative strand primers are used as mixtures; WD66, WD67 and WD155; or WD66, WD67, AND WD163; WD66, WD67, AND WD164, or most preferably, WD66, WD67, and WD154.

The negative strand primer WD154 was designed to hybridize to HPV31 DNA. Amplification of E6 sequences from HPV31 nucleic acids is improved when WD154 is included. Additional E6 consensus negative strand primers located in a different region of the gene, ~50 bp distal from WD66, WD67, and WD154, and are used in pairs as shown below to yield a 300 bp product. The three primer sets shown, WD157/WD160; WD158/WD161; and WD159/WD162, each correspond to the same genomic HPV region, but they differ in length and are HPV18 specific.

| | |
|---|---|
| WD157 | TTCTAMTGTWGTTSCATAYACASHATA |
| WD160 | CCAATGTGTCTCCATACACAGAGTC |
| WD158 | CTAMTGTWGTTSCATAYACASHATA |
| WD161 | AATGTGTCTCCATACACAGAGTC |
| WD159 | TAMTGTWGTTSCATAYACASHATA |
| WD162 | ATGTGTCTCCATACACAGAGTC | that comprises a portion of E7 DNA. To determine if amplification has occurred when the E6 consensus primers are used in the method of the invention, E6 consensus probes are provided. E6 consensus probes WD136 and WD135 are positive strand oligonucleotides directed to the small E6 amplification product and are used together as a mixture. The E6 consensus probes can also be used as E6 consensus positive strand primers. WD135 will hybridize to HPV6 and HPV11 DNA. WD136 is complementary to HPV types 16, 18, 33, and 39. When used as E6 consensus primers, the E6 consensus probes are used in the following combinations: WD65 and WD64; WD83 and WD64; and WD84 and WD64. The E6 consensus probes to two regions are depicted in Table 7.

TABLE 7

| E6 Consensus Probes for E6/E7 Product | | | | | | | | | | | | | | | | |
|---|---|---|---|---|---|---|---|---|---|---|---|---|---|---|---|---|
| WD65 | | M | G | A | G | A | C | R | G | C | W | W | T | C | C | A | T | W | T | G |
| WD83 | | M | G | A | G | A | C | R | G | S | W | W | T | C | C | A | T | W | T | G |
| WD84 | | M | G | A | G | A | C | R | G | V | W | W | T | C | C | A | T | W | T | G |
| WD64 | | A | G | A | G | A | C | R | G | T | A | T | A | C | C | G | C | A | T | G |
| HPV6 | 267 | C | G | A | G | G | C | G | G | C | T | A | T | C | C | A | T | A | T | G |
| HPV11 | 267 | — | — | — | — | A | — | A | A | — | — | T | — | — | — | C | — | T | — | — |
| HPV16 | 266 | A | — | — | — | A | T | — | I' | G | A | — | — | — | — | — | — | — | — | — |
| HPV18 | 273 | A | — | — | — | A | — | A | — | T | A | T | A | — | — | G | C | — | — | — |
| HPV33 | 271 | A | — | — | — | A | G | — | — | A | A | — | — | — | — | — | — | T | — | — |

| Consensus Probes for Detection of Small E6 Product | | | | | | | | | | | | | | | |
|---|---|---|---|---|---|---|---|---|---|---|---|---|---|---|---|
| MY135 (SEQ ID NO. 77) | | G | A | G | A | T | W | T | A | K | C | A | T | A | T | G | C |
| HPV6 | 225 | G | A | G | A | T | T | T | A | T | T | C | A | T | A | T | G | C |
| HPV11 | 225 | — | — | — | — | — | A | — | — | — | G | — | — | — | — | — | — | — |
| MY136 (SEQ ID NO. 78) | | G | A | G | G | T | A | T | W | T | G | A | H | T | T | T | G | C |
| HPV16 | 224 | G | A | G | G | T | A | T | W | T | G | A | H | T | T | T | G | C |
| HPV18 | 231 | — | — | — | — | — | — | — | T | — | — | — | A | — | — | — | — | — |
| HPV33 | 229 | — | — | — | — | — | — | — | — | — | — | — | T | — | — | — | — | — |
| HPV39 | | — | — | — | — | — | — | — | — | — | — | — | A | — | — | — | — | — |
| HPV45 | | — | — | — | — | — | — | — | — | — | — | — | A | — | — | — | — | — |

To determine the type of the HPV present in a sample when the E6 consensus primers are used in the method of the invention, E6 type-specific probes are provided. These probes are depicted in Table 8. Using URR/E6

| Predicted Sizes of Products from E6 Consensus Primers | | | | | | |
|---|---|---|---|---|---|---|
| | | Product Size for HPV Type | | | | |
| URR/E6 Primer | Downstream Primer | HPV6 | HPV11 | HPV16 | HPV18 | HPV33 |
| WD72 and WD73 | WD70 and WD71 | 770 | 770 | 802 | 844 | 791 |
| WD72 and WD76 | WD70 and WD71 | 770 | 770 | 802 | 844 | 791 |
| WD72 and WD77 | WD70 and WD71 | 770 | 770 | 802 | 844 | 791 |
| WD72 and WD73 | WD68 and WD69 | 758 | 758 | 790 | 832 | 779 |
| WD72 and WD76 | WD68 and WD69 | 758 | 758 | 790 | 832 | 779 |
| WD72 and WD77 | WD68 and WD69 | 758 | 758 | 790 | 832 | 779 |
| WD72 and WD73 | WD66 and WD67 | 243 | 243 | 242 | 242 | 225 |
| WD72 and WD76 | WD66 and WD67 | 243 | 243 | 242 | 242 | 225 |
| WD72 and WD77 | WD66 and WD67 | 243 | 243 | 242 | 242 | 225 |
| WD72 and WD76 | WD66, WD67, and WD154 | 243 | 243 | 242 | 242 | 225 |

Those skilled in the art will recognize that the E6 consensus primers of the invention amplify a sequence consensus primers comprising positive strand primers of Table 6 with WD70 and WD71 or WD68 and WD69 any of the HPV typing probes of Table 8 or Table 8A will be effective. These typing probes are also useful when E1 negative strand primers are used for amplification with the URR/E6 positive strand consensus primers.

amplification product of approximately 250 base pairs in length.

The present invention also provides primers that are complementary to sequences in the HPV E1 region. These E1 primers can be used to amplify only E1 region sequences or can be used in conjunction with E6/E7 primers to amplify sequences from E6, E7, E 1, and combinations of these three regions. These E 1 primers are shown below in Table 9.

TABLE 8

| HPV Typing Probes for Use with E6/E7 Amplified Sequences | | | |
|---|---|---|---|
| Probe | Specificity | Sequence | Genome Position |
| WD78 | HPV6 | 5' CGAAGTGGACGGACAAGAT | 643 |
| WD79 | HPV11 | 5' CAAGGTGGACAAACAAGACG | 643 |
| WD80 | HPV16 | 5' GAACACGTAGAGAAACCCAG | 534 |
| WD81 | HPV18 | 5' CAACCGAGCACGACAGGA | 530 |
| WD82 | HPV33 | 5' GAGGTCCCGACGTAGAGAA | 534 |

TABLE 8A

| HPV Typing Probes for Use with Small E6 Amplified Sequences | | | |
|---|---|---|---|
| Probe | Specificity | Sequence | Genome Position |
| WD165 | HPV31 | 5' AAATCCTGCAGAAAGACCTC | 116 |
| WD166 | HPV31 | 5' CCTACAGACGCCATGTTCA | |
| WD167 | HPV39 | 5' CCTTGCAGGACATTACAATAG | |
| WD168 | HPV39 | 5' CAGACGACCACTACAGCAA | |
| WD169 | HPV42 | 5' GGTGCAAAAAGCATTAACAG | |
| WD102 | HPV18 | 5' ACAGTATTGGAACTTACAG | 213 |
| WD103 | HPV16 | 5' CAACAGTTACTGCGACG | 206 |
| WD104 | HPV33 | 5' GCAGTAAGGTACTGCAC | 88 |
| WD132 | HPV18 | 5' GACAGTATTGGAACTTACAG | 213 |
| WD133 | HPV6 | 5' ACACCTAAAGGTCCTGTTTC | 248 |
| WD134 | HPV11 | 5' ACACTCTGCAAATTCAGTGC | 175 |
| RR1 (SEQ ID NO. 79) | HPV33 | 5' GTACTGCACGACTATGT | 96 |
| WD171 (SEQ ID NO. 80) | HPV45 | 5' ACAAGACGTATCTATTG | |
| WD170 (SEQ ID NO. 81) | HPV18 | 5' GCAAGACATAGAAATAA | 178 |
| RR2 (SEQ ID NO. 82) | HPV33 | 5' ACCTTTGCAACGATCTG | 212 |

The typing probes of Table 8A are useful with the positive strand URR, E6 consensus primers WD76/WD72 used with WD67, WD66 and WD 154; WD157 and WD160; WD158 and WD161; WD159 and WD162; WD66 and WD155; WD66 and WD163; and WD66 and WD164. These primers produce a small E6

TABLE 9

| E1 POSITIVE STRAND PRIMERS | | | | | | | | | | | | | | | | | | | | | | |
|---|---|---|---|---|---|---|---|---|---|---|---|---|---|---|---|---|---|---|---|---|---|---|
| TYP01 | 20MER | A | T | G | G | C | K | G | A | Y | C | C | T | G | M | A | G | G | T | A | C |
| TYP02 | 20MER | — | — | — | — | — | — | — | — | — | G | A | T | T | C | — | — | — | — | — | — |
| TYP03 | 20MER | — | — | — | — | — | — | — | — | — | C | C | T | T | C | — | — | — | — | — | — |
| TYP04 | 20MER | T | G | T | A | M | W | G | G | M | T | G | G | T | T | T | T | A | T | G | T |
| TYP05 | 20MER | — | — | — | — | — | — | — | — | — | — | — | — | — | — | — | G | A | G | — | — |
| TYP06 | 20MER | — | — | — | — | — | — | — | — | — | — | — | — | — | — | — | A | T | G | — | — |
| E1 NEGATIVE STRAND PRIMERS | | | | | | | | | | | | | | | | | | | | | | |
| TYN01 | 20MER | G | T | A | C | C | T | K | C | A | G | G | R | T | C | M | G | C | C | A | T |
| TYN02 | 20MER | — | — | — | — | — | — | G | A | A | T | C | — | — | — | — | — | — | — | — | — |
| TYN03 | 20MER | — | — | — | — | — | — | G | A | A | G | G | — | — | — | — | — | — | — | — | — |
| TYN04 | 20MER | A | C | A | T | A | A | A | A | C | C | A | K | C | C | W | K | T | A | C | A |
| TYN05 | 20MER | — | — | C | T | C | — | — | — | — | — | — | — | — | — | — | — | — | — | — | — |
| TYN06 | 20MER | — | — | C | A | T | — | — | — | — | — | — | — | — | — | — | — | — | — | — | — |
| TYN07 | 20MER | T | C | C | A | C | T | T | C | A | G | W | A | T | T | G | C | C | A | T | A |
| TYN08 | 20MER | — | — | — | — | — | — | — | — | — | — | — | — | Y | A | — | — | — | — | — | — |

These E1 primers can be used in a variety of embodiments of the present invention. For instance, amplifications wholly within the E1 region can be performed using the primer pairs: (1) TYP01, TYP02, TYP03, and TYN07, TYN08; or (2) TYP04, TYP05, TYP06 and TYN07, TYN08. Note that TYP03 is similar to both TYP02 and TYP01 and can be omitted from the amplification. The E1 region is highly conserved among HPVs, however, and although typing of the sample is possible with an E1 amplification, typing is more readily accomplished when the E1 primers are used in conjunction with E6 or E7 primers, as follows. For instance, one can amplify the E6/E7 region using the following E1 and E6/E7 primer pairs: (1) WD72, WD76 and TYN01, TYN02, TYN03; (2) WD64, WD65 and TYN01, TYN02, TYN03; (3) WD72, WD76 and TYN04, TYN05, TYN06; (4) WD64, WD65 and TYN04, TYN05, TYN06; (5) WD72, WD76 and TYN07, TYN08; and (6) WD64, WD65 and TYN07, TYN08. In these latter amplifications, the entire E7 region is amplified. Thus, these amplification products can be detected with the E7 consensus probes depicted below:

mids are non-essential aspects of the invention and numerous cloned HPVs are described in the literature.

Those skilled in the art recognize that the specific primers and probes disclosed herein are merely illustrative of the invention. For instance, because the primers and many of the probes of the invention are single-stranded DNA molecules, and because the target DNA (HPV DNA in a sample) is double-stranded DNA, useful primers and probes of the invention can be constructed merely by synthesizing primers and probes complementary to those specifically disclosed herein. The primers and probes of the invention can also be prepared to amplify and detect sequence variations within areas of HPV genomes other than those specifically exemplified herein.

Primers of the invention are generally 18 to 21 nucleotides in length and are designed to have a high degree of homology with HPV sequences. For instance, in the design of the genital HPV consensus primers of the invention, a high degree of homology with all five major genital HPVs (HPV types 6, 11, 16, 18, and 33) was required. The consensus primers also are highly homologous to HPV31 (Goldsborough et al., 1989,

| TYP09 | 5' | G | A | G | C | A | A | T | T | A | G | W | A | G | A | C |
|---|---|---|---|---|---|---|---|---|---|---|---|---|---|---|---|---|
| TYP12 | | — | — | — | — | — | — | — | — | — | A | R | Y | — | — | — |

In another aspect of the invention an internal amplification control is used to assure that the competency of a sample for amplification and reduce the likelihood of false negative results. The internal control can be a genomic segment of DNA known to be present in a sample of human origin. For example, the β-globin gene provides a suitable positive control amplification target. In one embodiment of the invention, β-globin primers are included in the PCR reaction mixture for amplifying the L1 region of the HPV genome. β-globin primers GH20 and PC04 produce a 268 base pair product.

(GH20 (Seq ID No. 83) 5'GAAGAGCCAAG-GACAGGTAC (PC04 (Seq ID No. 84) 5'CAACTTCATC-CACGTTCACC

The β-globin amplified segment is readily distinguished from the L1 amplified product by gel electrophoresis and by size (268 bp vs. 450 bp). For a positive control, when E6 consensus primers are used, other methods of detecting the β-globin product are desirable because the E6 product is 240 base pair in size and, therefore, is not necessarily easily distinguished. In that event, a β-globin probe can be used to detect the amplified product; PC03 is a suitable oligonucleotide probe.

PC03 (Seq ID No. 85) 5'ACACAACTGTGTT-CACTAGC

Alternatively, the β-globin and HPV amplification reactions can be run in parallel and analyzed individually. Similarly, it may be desirable to include positive and negative HPV controls in practicing the present methods for detecting and typing any HPV. For example, in one embodiment of the invention, plasmids containing genomic segments of HPVs 6, 11, 16, 18, and 33 are included. So long as the consensus primers, probes and type-specific probes used in the method can amplify and hybridize to the control nucleic acid, it is not essential that the control comprises the entire viral genome of each HPV. Example 2 describes specific HPV plasmids used as positive control; however, these specific plas- Virology 171:306–311). For each region to be amplified, two regions of homology are required, one for negative-strand primers and another for positive-strand primers. To identify a homologous region, viral sequences are compared. Once a homologous region is identified, a consensus primer is designed. Degenerate bases can be used in the design to accommodate positions at which an individual virus varies in sequence from the homologous sequence. As many degenerate positions are made as is necessary so that all viral sequences have fewer than three mismatches with the consensus primer. The degenerate positions are chosen so that the smallest number of degenerate bases accommodates the largest possible number of vital sequences.

If a particular vital sequence has a large number of mismatches with the consensus sequence, then a type-specific primer is made for that virus. The type-specific primer is mixed with the degenerate primer that was designed for other viruses to make the consensus primer. Any mismatches that are not accommodated by the degenerate positions in the primer should generally be located more than 3 bases from the 3' end of the primer. Likewise, any degenerate positions should be more than 3 bases from the 3' end of the primer.

Estimated minimum and maximum $T_m$s for a degenerate primer should be between 54 and 64 degrees C. $T_m$s are estimated by the non-empirical formula: each G or C contributes 4 degrees C. to the $T_m$; each A or T contributes 2 degrees C. to the $T_m$; and the $T_m$ is the sum of the calculated values. Finally, primers should not be designed to span palindromes or repetitive sequences.

Short oligonucleotide consensus probes design is similar to consensus primer design, except that consensus probes generally do not contain as many mismatches as consensus primers. As a result, the $T_m$ for a probe can be higher than the $T_m$ for a primer. However, where a mismatch or degenerate position occurs with respect to the 3' end is not as critical for consensus probes as it is for consensus primers. Clearly, long probes can tolerate a greater number of mismatches because of the overall length of the probe.

Type-specific probes are designed so that a given probe will generally have less than 75% similarity with sequences from HPV types distinct from that recognized by the probe. The type-specific probes are usually 18–20 nucleotides in length with estimated $T_m$s in the range of 58 to 64 degrees C. The present invention also describes that more than one type-specific probes may be employed for typing. This aspect of the invention provides additional assurance that variant types will be correctly detected and typed. Preferably two type specific probes are employed that are capable of hybridizing to opposite strands and residing in separate regions of the amplified product.

Those skilled in the art also recognize from the present disclosure that the method of the present invention can be carried out in a variety of ways. The present method is applicable to any human papillomavirus and especially preferred for detecting and typing genital HPVs. The method can be used to detect isolate-to-isolate variation within a particular HPV type and can also be used to screen for significant changes in the HPVs present in a patient. In one embodiment of the invention, consensus primers to more than one region of HPV DNA will be used, ensuring that if any portion of the HPV genome has been deleted, other regions can still be detected. In a similar fashion, the typing of the amplified DNA can be done using a variety of type-specific probes that recognize different regions of the amplified DNA. In a preferred embodiment, probes capable of hybridizing to at least two regions of the amplified DNA are employed to increase the likelihood of typing correctly HPV variants.

Those skilled in the an recognize that the present invention can also be used to detect HPV mRNA present in a sample. The expression of certain HPV mRNA species, particularly E6 and E7 mRNAs, may be indicative of the likelihood than an HPV infection will progress to carcinoma. To detect an HPV mRNA by the method of the present invention, the mRNA can be treated with reverse transcriptase in an appropriate reaction mixture to synthesize a cDNA molecule. The primer used in the reverse transcription reaction can be a consensus primer of the invention or can be a different oligonucleotide that hybridizes near the 3' end of the mRNA. Although random hexamers are not specific for the 3' end of the molecule, they are suitable for reverse transcription of RNA to provide a cDNA template for amplifying HPV nucleic acids. This cDNA copy is then made into a double stranded DNA molecule, which can be detected and typed in accordance with the method of the present invention.

The consensus primers of the present invention can also be used to detect HPV types previously uncharacterized. For instance, HPV isolate 88 noted in Table 4, above, has previously not been reported. Thus, the consensus primers of the invention can be used to amplify DNA sequences of previously unknown HPV types. The amplified DNA can then be sequenced and the sequence data used to generate type-specific probes for use in the method of the present invention.

The present invention may be assembled as a kit for detecting and typing HPV. Such a kit would include consensus primers and type-specific probes. A preferred kit also includes means for determining if amplification has occurred, such as a consensus probe or long probe. Additional kit components may include and are not limited to any of the following: PCR buffers and enzymes; positive control HPV or non-HPV DNAs; positive control primers, for example, β-globin primers; a positive control probe; primers for preparing long probes; means for detecting hybridized probes; and instructions for amplifying, detecting, and typing HPV.

The examples provided below merely illustrate the invention and in no way limit the scope of the accompanying claims.

EXAMPLE 1

PCR-Based Detection and Typing of HPV

Preparation of Clinical Samples for PCR

The disclosed methods for detecting and typing HPV in a clinical sample are suitable for use with any sample that is suspected of containing HPV nucleic acids. It will be apparent to one of ordinary skill in the an that sample preparation procedures vary according to sample source. Specific examples are provided for sample preparation from a variety of sources.

A. Samples collected in ViraPap ™ (Life Technologies Inc.) collection tubes were digested according to manufacturer's instructions. Samples were handled with extreme care to avoid cross-contamination (Kwok, 1989, *Nature* 339:237–238). Two hundred microliters of each sample was removed for PCR analysis with a disposable pipet, precipitated at $-20°$ C. overnight with 2M ammonium acetate and 70% ethanol, dried, and resuspended in 20 μl TE (10 mM Tris-HCl, pH 7.5, 1mM EDTA). Two μl and 5 μl aliquotes were used for each amplification reaction. ViraPap ™ collection tubes containing known amounts of purified human genomic DNA from the K562 cell line (ATCC #CCL243), which does not contain HPV DNA, were processed with each batch of 20 samples to monitor possible contamination in sample processing. The K562 cell line provided a negative control.

B. Freshly collected cells from clinical swabs were suspended in 1 ml of saline, pelleted by centrifugation, and the supernatant discarded. If cell suspensions were to be stored for a period of time before the test, antibiotics were generally added to the suspension (a commercially available antibiotic, such as Fungi Bact Solution, is suitable for this purpose). The cell number was estimated, and if blood was present in the sample, the cells were suspended in 1 ml of TE buffer to lyse the red blood cells and then repelleted. About $10^2$–$10^4$ cells were used for each PCR. The cells were first suspended in 100 μl of buffer containing 50 mM Tris, pH 8.5; 1 mM EDTA; 1% Laureth-12; and 200 μg/ml proteinase K. This mixture was incubated at 55 degrees C. for about 1 hour, and then the proteinase K was heat-inactivated by incubating the mixture at 95 degrees C. for 10 minutes. Aliquots containing $10^2$–$10^4$ cells were used per 100 μl of mixture containing proteinase K treated cells.

C. Cervicovaginal lavage samples were stored frozen in 0.9% saline. For PCR the samples, as 1 ml aliquots, were thawed and mixed gently. Fifty microliters of sample was removed with a disposable piper and added to 50 μl of 2X digestion solution in a labeled tube. The digestion solution was prepared fresh (1X digestion solution comprises 200 μg/ml proteinase-K, 1% Laureth-12, 20 mM Tris-HCl pH 8.5, and 0.4 mM EDTA). The samples were incubated for one hour at 55° C., spun briefly, and placed at 95° C. for 10 minutes to heat inactivate the protease. The samples were again spun briefly and 5–10 μl of each sample was added to a PCR mix for a 100 μl PCR reaction.

D. The method of the present invention will often be used to determine whether tissue sections in paraffin contain HPV. To prepare such a tissue section, typically 5–10 μM in width, for use in the present method, the following procedure was employed. The tissue section was extracted twice with 1 ml of octane to remove the paraffin. Each extraction was for about one-half hour. The tissue section was then rinsed twice with 100% ethanol to remove the extracting agent and dried. The section was then suspended in buffer with detergents and proteinase K and (200 μg/ml proteinase-K, 1% Laureth-12, 50 mM Tris-HCl pH 8.5, and 1 mM EDTA) and incubated at 55° C. for 2–4 hours. After heat inactivation of the proteinase K, the suspension was centrifuged to pellet debris, and about 1–20 μl of the supernatant were used for each PCR reaction.

Control DNAs

HPV DNAs used in control amplifications were either recombinant plasmids containing HPVs (6, 11, 16, 18, 31, 33, 39, and 45) or DNA from cell lines containing HPVs (HPV16: SiHa [ATCC no. HTB35] or Caski [ATCC no.CRL 1550]; and HPV18: HeLa [ATCC no. CCL2]). DNA from the K562 cell line (ATCC no. CCL243) served as an HPV-negative control. Cellular DNA (3 to 15 ng) or plasmid DNA (1–10 pg) was used in control amplifications. Products from these amplifications were used to assess the specificity of type-specific probes.

PCR Protocols

All PCR protocols were carded out using a Perkin-Elmer/Cetus Instruments Thermal Cycler instrument. A typical reaction mixture contained 50 pmoles each L1 consensus primer MY09 and MY 11; 2.5 units of Taq polymerase; 10 μl of 10X PCR buffer (0.5M KCl; 100 mM Tris, pH 8.5; 40 mM $MgCl_2$); 0.2 mM of each dNTP; 1–20 μl of each clinical, cell, or paraffin sample; and deionized water to 100 μl. A 100 μl mineral oil overlay was added to each reaction to avoid evaporation. When an amplification control was included in the reaction, 5 picomoles of each β-globin primer (PC04 and GH20) (Seq ID Nos. 83 and 84) was added to the reaction mix.

Because of the extreme sensitivity of PCR, the potential exists for false positive results arising from sample cross-contamination or PCR product carry-over. Extreme care was taken to prevent contamination. Only disposable or positive displacement pipets were used in sample handling and PCR set-up. In addition, pre- and post-PCR samples and reagents were kept separated throughout all stages of the work. The extensive use of negative controls support the conclusion that contamination did not occur at any point in sample handling and all positive results represent true vital presence.

The clinical or cell sample aliquot was added immediately before temperature cycling. Tubes containing the K562 negative control DNA or no added DNA were included. PCR reaction times for use with clinical samples were as follows. The machine was heated to 85° C. before the samples were placed into the machine. The machine was then programmed to execute the following temperature changes: 35 cycles of 60 seconds at 95° C., 60 seconds at 55° C. and 60 seconds at 72° C.; 5 minutes at 72° C.; and then hold at 15° C.

For paraffin sections, the machine was programmed to reach 85° C. and execute temperature changes as follows: forty cycles of 60 seconds at 95° C., 60 seconds at 55° C., and 2 minutes at 72° C.; then 5 minutes at 72° C.; and then hold at 15° C. The MY09, MY 11 PCR product is less than 600 base pairs; however, if alternative primers were used and the PCR product was expected to be longer than 600 base pairs, the machine was programmed to execute temperature changes as follows: 1 minute at 85° C.; forty cycles of a 50 second ramp to 95° C., 50 seconds at 95° C., a 50 second ramp to 55° C., 50 seconds at 55° C., a 50 second ramp to 72° C., and 2 minutes at 72° C.; 5 minutes at 72° C.; and then hold at 15° C.

Following amplification, 5 μl of each completed reaction was electrophoresed on a 7% polyacrylamide gel, ethidium bromide stained, and photographed. Dot blots of each PCR amplification reaction were prepared.

Generic HPV Probe

A generic HPV probe was synthesized from 450 bp L1 PCR fragments of HPV16 (Caski), HPV18 (HeLa), PAP238B (a cloned clinical sample identified as HPV31) and a highly divergent, unidentified HPV sequence that was previously isolated and cloned from clinical specimens and is referred to here in as PAP88. PCR amplifications were performed separately using nested primers (Seq ID No. 1/Seq ID No. 2) MY74/MY75 for HPV16; MY76/MY77 (Seq ID No. 3/Seq ID No. 4) for HPV18; MY47/MY48 (Seq ID No. 5/Seq ID No. 6) for PAP88; and MY49/MY50 (Seq ID No. 7/Seq ID No. 8) for PAP238B. The L1 amplification products were used as the templates for preparing the generic probes. The buffer and enzyme conditions were used as described above except that the final 50 μl PCR contained 50 μM each dNTP, 62.5 pmol (50 μCi) each $\alpha$-$^{32}$P-labeled dNTP, and 20 picomoles of each primer. The mineral oil overlay was omitted and the PCR cycling program was as follows: 30 seconds at 95° C., 30 seconds at 55° C., 1 minute at 72° C. for 25 cycles with a final 5 minute extension at 72° C. The PCR products from identical unlabeled reactions were visualized using electrophoresis and ethidium bromide staining. The labeled ~400 bp fragments were purified using a G50 Sephadex column, and the cpm of the probes was determined using a scintillation counter. The four probes were denatured at 95° C. for 10 minutes in the presence of sheared salmon sperm DNA, then rapidly cooled in a dry ice/ethanol bath before addition to the hybridization solution. Membranes were hybridized with a mixture of 1.0–1.5 × $10^5$ cpm/ml of each probe.

Hybridization Analysis of PCR Products

To determine if amplification had occurred the following protocol was used. About 2 μl of each reaction mixture were added to 100 μl of denaturing solution (0.4M NaOH and 25 mM EDTA) for each replicate dot and spotted onto replicate, positively-charged, nylon membranes (such as Genetran 45, Biodyne B Membrane [Pall], or Biotran from ICN) using a dot-blot or slot blot apparatus. The resulting dot was rinsed once with 200 μl of 20XSS C. The membrane was then removed from the blotter, air-dried, and exposed to ultraviolet light (with the DNA facing the light) to covalently attach the DNA to the membrane (50 mjoules) by using a commercial UV crosslinking apparatus. Amplified L1 fragments from HPV types 6, 11, 16, 18, 31, 33, 35, 39, and 45 were spotted onto each membrane as positive controls to assess cross-hybridization and optimize exposure times.

The membrane was pre-hybridized at least 30 minutes at 65° C. in a water bath or air incubator. The pre-hybridization solution contained 6XSSC, 5X Denhardt's solution, and 0.1% SDS and 100 μg/ml denatured salmon sperm DNA. Alternatively, the membranes can merely be rinsed with pre-hybridization solution. $^{32}$P-labeled consensus probes (1.0–1.5×10$^5$ cpm/ml of hybridization mix) were added to each filter and allowed to hybridize at 55° C. for at 60–90 minutes. After the hybridization, the hybridization mix was decanted and the membrane was washed twice for 10 minutes in 2XSSC and 0.1% SDS at 56° C. for the HPV generic and β-globin probes. The membrane was then air-dried and allowed to expose X-ray film from 7 to 48 hours. Background was defined by negative controls which included amplified human genomic DNA.

To determine the HPV type of amplified DNA, PCR reaction mixtures were hybridized to type-specific probes as described above. The only significant difference in the procedure was that the final wash of the filter was done at a temperature very near the $T_m$ of the particular type-specific probe. Filters hybridized to different type-specific probes were not washed together. Specifically, membranes were hybridized individually with probes for HPV types 6/11, 16, 18, 31, 33, 39, 45, 51, 52, and 53, and PAP88, PAP155, and PAP251 as listed below. Type-specific oligonucleotide probes were $^{32}$P-labeled using a standard kinase reaction (Maniads et al. eds. Molecular Cloning, 1982, Cold Spring Harbor, N.Y.). Membranes were pre-hybridized and hybridized as described above, then washed as follows:

| Probe | Target | Wash Temperature |
| --- | --- | --- |
| MY12 | HPV6 | 57° C. |
| MY13 | HPV11 | 57° C. |
| MY14 | HPV16 | 59° C. |
| WD74 | HPV18 | 59° C. |
| WD126 | HPV31 | 57° C. |
| WD128 | HPV31 | 57° C. |
| MY16 | HPV33 | 57° C. |
| MY59 | HPV33 | 57° C. |
| MY89 (SEQ ID NO. 32) | HPV39 | 58° C. |
| MY90 (SEQ ID NO. 33) | HPV39 | 58° C. |
| MY70 | HPV45 | 59° C. |
| MY98 (SEQ ID NO. 43) | HPV45 | 59° C. |
| MY87 (SEQ ID NO. 48) | HPV51 | 58° C. |
| MY88 (SEQ ID NO. 49) | HPV51 | 58° C. |
| MY81 (SEQ ID NO. 51) | HPV52 | 57° C. |
| MY82 (SEQ ID NO. 52) | HPV52 | 57° C. |
| MY101 (SEQ ID NO. 53) | HPV53 | 58° C. |
| MY102 (SEQ ID NO. 54) | HPV53 | 58° C. |
| MY103 (SEQ ID NO. 55) | HPV53 | 58° C. |
| MY83 (SEQ ID NO. 68) | PAP88 | 58° C. |
| MY84 (SEQ ID NO. 69) | PAP88 | 58° C. |
| MY86 (SEQ ID NO. 70) | PAP155 | 58° C. |
| MY93 (SEQ ID NO. 72) | PAP251 | 58° C. |
| MY94 (SEQ ID NO. 73) | PAP251 | 58° C. |

Autoradiogram exposures that gave an intensity comparable to the generic probe were analyzed using the same standards described above. The sensitivity of this method was 100 copies of cloned HPV16 DNA or 10 HeLa cells containing 100–500 copies of HPV-18, per 1 ml collection tube when 2–5% was analyzed.

EXAMPLE 2

Dual Amplification of Archival Samples

A second set of consensus primers was designed to amplify a region of the E6 gene approximately 246 bp in length. These consensus primers were used in addition to the L1 consensus primers described in Example 1. The second set provides a means to generate corroborative HPV typing data and focuses on a gene which is consistently retained and expressed in tumors (Yee et al., 1985, Am. J. Pathol. 116:361–366; Seedoff et al., 1987, EMBO 6:139–144; and Broker et al., In Cancer Cells: Molecular Diagnostics of Human Cancer, vol. 7, Cold Spring Harbor, N.Y., 1989, pp. 197–208).

Archival tissue sections, which included 33 cases of cervical carcinoma, were subjected to PCR amplification with the L1 and E6 primer sets. The resulting products were analyzed by dot blot hybridization with consensus and type-specific oligonucleotide probes to illustrate the efficacy of the two site amplification strategy in the detection and typing of genital HPVs.

Tumor Samples

Sections from 48 paraffin-embedded tissue blocks representing 33 cases of cervical carcinoma and 7 HPV-negative control tissues were acquired from the pathology archives at the University of Amsterdam, the University of California at San Francisco, and the University of California at Davis. The case dates ranged from 1979 to 1988. Five micron sections were cut from tissue blocks with a microtome and the microtome blade was thoroughly cleaned with xylene between each specimen to minimize cross-contamination of samples. Dry sections were transferred to eppendorf tubes for PCR analysis and immediately adjacent sections were mounted and stained with hematoxylin and eosin for independent histological characterization. Preparation of DNA from tissue sections for PCR was done as described in Example 1.

HPV-negative tissues were interspersed with tumor samples during tissue preparation to detect any possible contamination during sample manipulation. The prepared samples were used immediately for PCR amplification, although storage at 20° C. for up to two weeks resulted in only a nominal loss in specific amplification product yield. Control DNAs, described in Example 1, were included as specified below in the section "Dot Blot Hybridization of PCR Products."

PCR Amplification

L1 and E6 amplification reactions were performed using 1 and 10 μl (0.5% and 5%) of each prepared sample. In addition to HPV-negative and HPV-positive control samples, "no DNA" controls were included during each amplification series to detect contamination during reaction set-up. Furthermore, only positive displacement pipets and disposable pipets were used in the assembly of amplification reactions to minimize possible contamination.

Each L1 amplification reaction contained 50 pmoles each of the L1 degenerate primers MY11 and MY09 as described (Example 1 ) and 5 pmoles each of the β-globin primers GH20 (Seq ID No. 83) (5'GAAGAGC-CAAGGACAGGTAC) and PC04 (Seq ID No. 84) (5'CAACTTCATCCACGTTCACC) was included for the simultaneous amplification of a human β-globin product of 260 bp which served as an internal control.

The E6 reactions included 10 pmoles WD72 and 40 pmoles WD76 (the positive strand primers) and 10 pmoles WD66, 40 pmoles WD67, and 10 pmoles WD 154 (the negative strand primers) in a buffer containing 50 mM KCl, 10 mM Tris (8.3), 4 mM MgCl$_2$, 200 μM of each dNTP and 2.5 units of the recombinant AmpliTaq ® polymerase (Perkin-Elmer Cetus Instruments).

Each reaction was subjected to forty amplification cycles in a DNA Thermal Cycler (Perkin Elmer Cetus Instruments) using thermocycle step parameters of 95° C. for 1 minute, 55° C. for 1 minute and 72° C. for 2 minutes. An additional five minutes was included at the final 72° C. elongation cycle. Thirty cycles were used in the amplification of HPV positive control DNA. Amplification products (1/20 of the reaction) were separated by electrophoresis using 7% polyacrylamide gels and visualized by UV illumination following ethidium bromide staining.

Probes

Oligonucleotide probes used for the dot blot hybridizations were labeled to a specific activity of 0.3-1X $10^7$ cpm/pmole with $\alpha$-$^{32}$P ATP using T4 polynucleotide kinase (NENuclear/du Pont).

The consensus L1 probe was an equimolar mixture of the following four oligonucleotides corresponding to a conserved region located 50 base pairs (bp) from the 5'end of amplified region:

MY18 (5'CTGTTGTTGATACTACACGCAG-TAC);
MY46 (Seq ID No. 9) (5'CTGTGGTAGATAC-CACWCGCAGTAC);
MY57 (5'CTGTGGTAGATACCACACGTAG-TAC); and
WD 147 (5'CTGTAGTGGACACTACCCGCAG-TAC).

L1 type-specific probes were MY12 for HPV6, MY13 for HPV11, MY14 for HPV16, WD74 for HPV18, WD126 and WD128 for HPV31, MY16 and MY59 for HPV33 and MY70 for HPV45. MY12 and MY13 were used together as a mixture to detect both HPV6 and 11. In clinical practice it is not necessary to separate HPV6 and HPV 11 type specific probes because these HPVs are highly related in sequence and in pathogenic potential. HPV6 and HPV11 are most often associated with benign lesions.

The use of two type specific probes for each HPV type provides additional assurance that all HPV DNAs will be typed correctly including variants, where nucleotide changes in the region of one type specific probe have occurred, will not be mistyped. Probes WD126, WD128, and WD170 (Seq ID No. 81) were designed using sequence information generated from amplification products of clinical isolates which were subsequently identified as HPV31 and HPV45. WD128 and WD126 reside in separate domains on the L1 product. WD128 detects both HPV31 and a variant referred to as HPV31b. The sequence of the HPV31b L1 product contains a restriction site not present in the archetypic HPV31. PC03 (Seq ID No. 85) (5'ACA-CAACTGTGTTCACTAGC) was used to identify the $\beta$-globin product according to Example 1.

Oligonucleotide probes designed to distinguish E6 products were: WD 133 for HPV6, WD134 for HPV11, WD103 for HPV16, WD132 and WD170 (Seq ID No. 81) for HPV18, WD165 and WD166 for HPV31, RR1 and RR2 (Seq ID Nos. 79 and 82) for HPV33, and WD171 (Seq ID No. 80) for HPV45. The sequence of the HPV45 E6/E7 region was determined from pHPV45 kindly provided by K. Shah (Johns Hopkins University).

Dot Blot Hybridization of PCR Products

Replicate dot blots were prepared using 1/50 (2 $\mu$l) of each amplification reaction. Additionally, control reactions (HPV positive SiHa DNA, HPV negative K562, and "no DNA") from each amplification series were included. Two $\mu$l of each reaction were denatured in 100 $\mu$l of 0.4N NaOH, 25 mM EDTA for each dot, applied to a Gentran 45 membrane (Hasco, Inc), and covalently bound by UV linking using a Stratalinker (Stratagene, Inc.) at 400 (X 100) $\mu$Joules. The filters were washed in 0.1 X SSC, 0.5% SDS at 60° C. for 30 minutes, followed by prehybridization for 15 minutes at 55° C. with 6 X SSC, 5 X Denhardt's solution 0.5% SDS, 100 g/ml single-stranded sheared salmon sperm DNA.

Replicate filters were separately hybridized with $^{32}$P-labeled type-specific and generic oligonucleotide probes (1–200,000 cpm/ml) in 6 X SSC, 5 X Denhardt's solution 0.5% SDS, 100 $\mu$g/ml single-stranded sheared salmon sperm DNA for 1 hour at 55° C. Probes WD170 and WD171 (Seq ID Nos. 80 and 81) required hybridization at 45° C.

Filters were rinsed briefly in 2 X SSC, 0.1% SDS at room temperature and then twice for 10 minutes at 45° C. (WD170 and WD171) [Seq ID Nos. 80 and 81]); 50°–52° C. (WD132, RR1 and RR2[Seq ID Nos. 79 and 82]), 55°–56° C. (the consensus L1 probe mix, WD103, WD132, WD165, and WD166); 56°–57° C. (MY12-/MY13, WD126, MY16, MY70, and WD133/WD134); or 58°–59° C. (MY14, WD128, MY59/MY64, MY70, and WD74). The membranes were subjected to autoradiography using Kodak XAR-5 film. L1 and E6 dot blot results were scored independently. The results indicated that for HPV45, MY69 may be a preferred type-specific probe, because MY70 has some sequence similarity to other HPVs.

Bands of predicted size for E6 or L1 were not detected in reactions from the normal cervical tissues nor an appendix. PCR products of the expected size for an L1 product were observed in all tumor samples with the exception of one of the older samples in the collection. Typing results with the E6 and L1 products were in complete agreement in all cased examined, except for one specimens which failed to produce an L1 PCR product. The single L1-negative specimen found in this study illustrates the value of a strategy based on two site analysis.

Other modifications of the embodiments of the invention described above that are obvious to those of ordinary skill in the areas of molecular biology, medical diagnostic technology, biochemistry, virology, genetics and related disciplines are intended to be within the scope of the accompanying claims.

EXAMPLE 3

Preparation of the Biotinylated Long Probes

In a non-isotopic detection format, Bio-11 (dUTP) (Sigma #B7645) was incorporated into the long L1 probe instead of $^{32}$P dNTP. Subsequent detection of the probe utilized a SA-HRP binding step and development of signal with Amersham's Enhanced ChemiLuminescence (ECL) system.

All reactions contained 2 $\mu$l of a 1:100 or 1:1000 dilution of the appropriate MY09/MY11 generated L1 PCR product, 50 mM KCL, 10 mM Tris, pH 8.5, 2.5 units Taq polymerase, 200 $\mu$M dATP, dCTP, dGTP, 100 $\mu$M dTTP and 100 $\mu$M Bio-11 dUTP. The primer and MgCl$_2$ concentrations varied as follows: MY47 and MY48, 10 picomoles per primer and 4 mM MgCl$_2$; MY49 and MY50(Seq ID Nos. 7 and 8), 10 picomoles each primer and 6 mM MgCl$_2$; MY74 and MY75 (Seq ID Nos. 1 and 2), 10 picomoles each primer and 4 mM MgCl$_2$; MY76 and MY77 (Seq ID Nos. 3 and 4), 50 picomoles each primer and 8 mM MgCl$_2$. Each reaction was 200 $\mu$l in volume with a 100 $\mu$l mineral oil overlay. Thermal cycling parameters were 30 seconds at 95° C., 30 seconds at 55° C. and 1 minute at 72° C. with a five minute extension at 72° C. at the end of 30 cycles. The biotinylated PCR product was purified using a G50 Sephadex column (eluted with TE and 0.2% SDS) or an isopropanol, 2M ammonium acetate precipitation. Aliquots of both biotinylated and non-biotinylated long probes were electrophoresed on 7% acrylamide gels, ethidium bromide stained, and photographed under UV light. The non-biotinylated probe migrated further than the biotinylated probe.

The hybridization protocol using biotinylated probes was as described in Example I. Amersham's ECL system was used for detection according to the manufacture's instructions; however, the mount of SA-HRP used at the binding step was tinted for each lot of reagent.

Other modifications of the embodiments of the invention described above, that are obvious to those of ordinary skill in the areas of molecular biology, medical diagnostic technology, biochemistry, virology, genetics, and related disciplines, are intended to be within the scope of the invention and the accompanying claims.

We claim:

1. A method for detecting any one or more of human papillomavirus (HPV) type 5, 6, 8, 11, 16, 18, 26, 27, 30, 31, 33, 35, 39, 40, 41, 42, 43, 45, 47, 48, 51, 52, 53, 54, 55, 57, 58, or 59 nucleic acids in a sample that comprises the steps of:

(a) treating said sample under conditions for amplifying a nucleic acid sequence in an amplification reaction mixture that comprises a consensus HPV primer pair, wherein said consensus HPV primer pair consists of MY09 and MY11, to provide an amplified nucleic acid sequence if said HPV nucleic acid is present, and (b) detecting said HPV nucleic acid by determining if amplification has occurred.

2. The method of claim 1, wherein at step (b) said amplified nucleic acid sequence is detected by hybridization to a consensus probe composition which composition comprises an equimolar mixture of oligonucleotides MY18, MY46, MY57 and WD147.

3. The method of claim 1, wherein at step (b) said amplified nucleic acid sequence is detected by hybridization to an oligonucleotide probe selected from the group consisting of: MY12, MY62, MY63, MY125 (Seq ID No. 10), MY126 (Seq ID No. 11), MY13, MY61, MY65, WD150, WD151, MY14, MY58, MY71 (Seq ID No. 12), MY72 (Seq ID No. 13), MY95 (Seq ID No. 14), MY96 (Seq ID No. 15), MY97 (Seq ID No. 16), MY133 (Seq ID No. 17), WD152, WD153, MY60, MY73 (Seq ID No. 18), MY107 (Seq ID No. 19), MY130 (Seq ID No. 20), MY131 (Seq ID No. 21), MY132 (Seq ID No. 22), WD74, WD75 (Seq ID No. 23), WD126, WD127, WD128, MY109 (Seq ID No. 24), MY110 (Seq ID No. 25), MY92 (Seq ID No. 26), MY127 (Seq ID No. 27), MY128 (Seq ID No. 28), MY16, MY59, MY64, MY115 (Seq ID No. 29), MY116 (Seq ID No. 30), MY117 (Seq ID No. 31), MY89 (Seq ID No. 32), MY90 (Seq ID No. 33), MY91 (Seq ID No. 34), MY118 (Seq ID No. 35), MY119 (Seq ID No. 36), MY120 (Seq ID No. 37), MY121 (Seq ID No. 38), MY122 (Seq ID No. 39), MY33 (Seq ID No. 40), MY34 (Seq ID No. 41), MY68 (Seq ID No. 42), MY69, MY70, MY98 (Seq ID No. 43), MY99 (Seq ID No. 44), MY100 (Seq ID No. 45), MY108 (Seq ID No. 46), MY129 (Seq ID No. 47), MY87 (Seq ID No. 48), MY88 (Seq ID No. 49), MY80 (Seq ID No. 50), MY81 (Seq ID No. 51), MY82 (Seq ID No. 52), MY101 (Seq ID No. 53), MY102 (Seq ID No. 54), MY103 (Seq ID No. 55), MY111 (Seq ID No. 56), MY112 (Seq ID No. 57), MY113 (Seq ID No. 58), MY114 (Seq ID No. 59), MY151 (Seq ID No. 60), MY152 (Seq ID No. 61), MY153 (Seq ID No. 62), MY154 (Seq ID No. 63), MY155 (Seq ID No. 64), MY156 (Seq ID No. 65), MY123 (Seq ID No. 66), MY124 (Seq ID No. 67), MY83 (Seq ID No. 68), MY84 (Seq ID No. 69), MY86 (Seq ID No. 70), MY85 (Seq ID No. 71), MY93 (Seq ID No. 72), MY94 (Seq ID No. 73), MY104 (Seq ID No. 74), MY105 (Seq ID No. 75), MY106 (Seq ID No. 76), MY66, MY55, MY39, MY56, MY57, MY46, and WD147.

4. A method for detecting any one or more of human papillomavirus (HPV) type 5, 6, 8, 11, 16, 18, 26, 27, 30, 31, 33, 35, 39, 40, 41, 42, 43, 45, 47, 48, 51, 52, 53, 54, 55, 57, 58, or 59 nucleic acids in a sample that comprises the steps of:

(a) treating said sample under conditions for amplifying a nucleic acid sequence in an amplification reaction mixture that comprises a pair of consensus HPV primers, wherein said consensus HPV primers consist of positive and negative strand primers and said positive primers are selected from the group consisting of: WD72/WD73, WD72/WD76, WD72/WD77, WD65/WD64, WD83/WD64, and WD84/WD64; and said negative strand primers are selected from the group consisting of WD70/WD71; WD86/WD69; and WD66/WD67; to provide an amplified nucleic acid sequence if said HPV nucleic acid is present, and (b) detecting said HPV nucleic acid by determining if amplification has occurred.

5. The method of claim 4, wherein at step (b) said amplified nucleic acid sequence is detected by hybridization to a consensus probe selected from the group consisting of: WD64, WD65, WD83, WD84, MY135 and MY136.

6. The method of claim 4, wherein at step (b) said amplified nucleic acid sequence is detected by hybridization to an oligonucleotide probe selected from the group consisting of: WD78, WD79, WD80, WD81, WD82, WD165, WD166, WD167, WD168, WD169, WD104, WD102, WD103, WD132, WD133, WD134, $RR_1$ (Seq ID No. 79), RR2 (Seq ID No. 82), WD170 (Seq ID No. 81), WD171 (Seq ID No. 80).

7. A method for detecting any one or more of human papillomavirus (HPV) type 5, 6, 8, 11, 16, 18, 26, 27, 30, 31, 33, 35, 39, 40, 41, 42, 43, 45, 47, 48, 51, 52, 53, 54, 55, 57, 58, or 59 nucleic acids in a sample that comprises the steps of:

(a) treating said sample under conditions for amplifying a nucleic acid sequence in an amplification reaction mixture that comprises a consensus HPV primer pair, wherein said consensus HPV primers consist of oligonucleotides selected from the group consisting of: WD64/WD65 and TYN01/TYN02/TYN03; WD64/WD65 and TYN04/TYN05/TYN06; WD64/WD65 and TYN07/TYN08; WD72/WD76 and TYN01/TYN02/TYN03; WD72/WD76 and TYN04/TYN05/TYN06; WD72/WD76 and TYN07/TYN08; TYP01/TYP02 and TYN07/TYN08; and TYP04/TYP05/TYP06 and TYN07/TYN08; to provide an amplified sequence if said HPV nucleic acid is present, and (b) detecting said HPV nucleic acid by determining if amplification has occurred.

8. The method of claim 7, wherein at step (b) said amplified nucleic acid sequence is detected by hybridization to an oligonucleotide probe selected from the group consisting of: TYP09 and TYP12.

* * * * *